(12) United States Patent
Moritsugu et al.

(10) Patent No.: US 7,073,320 B2
(45) Date of Patent: Jul. 11, 2006

(54) FAULT DETECTING APPARATUS DESIGNED TO DETECT DIFFERENT TYPES OF FAULTS OF GAS SENSOR

(75) Inventors: Michiyasu Moritsugu, Okazaki (JP); Takanao Tomura, Nishio (JP); Keigo Mizutani, Okazaki (JP); Daisuke Makino, Ichinomiya (JP); Eiichi Kurokawa, Okazaki (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 172 days.

(21) Appl. No.: 10/841,493

(22) Filed: May 10, 2004

(65) Prior Publication Data

US 2004/0221641 A1  Nov. 11, 2004

(30) Foreign Application Priority Data

May 9, 2003  (JP) .............................. 2003-131749

(51) Int. Cl.
 *F01N 3/00* (2006.01)
(52) U.S. Cl. .................. 60/276; 60/277; 60/285; 123/688; 73/23.32; 73/23.33; 73/118.1; 701/107; 701/115
(58) Field of Classification Search .................. 60/274, 60/276, 277, 285; 123/688, 690; 73/23.31, 73/23.32, 23.33; 701/107, 109, 115
See application file for complete search history.

(56) References Cited

U.S. PATENT DOCUMENTS

| | | | |
|---|---|---|---|
| 4,777,922 A | 10/1988 | Mieno et al. | |
| 4,951,632 A | 8/1990 | Yakuwa et al. | |
| 5,386,695 A * | 2/1995 | Iwata et al. | 60/276 |
| 5,526,798 A * | 6/1996 | Seki | 123/688 |
| 5,925,088 A | 7/1999 | Nasu | |
| 6,136,169 A | 10/2000 | Okamoto | |
| 6,341,599 B1 * | 1/2002 | Hada et al. | 123/688 |
| 6,343,499 B1 | 2/2002 | Inagaki et al. | |
| 6,901,741 B1 * | 6/2005 | Kobayashi et al. | 60/274 |
| 6,920,751 B1 * | 7/2005 | Yasui et al. | 60/277 |
| 2002/0175086 A1 | 11/2002 | Nakamichi et al. | |

FOREIGN PATENT DOCUMENTS

| | | |
|---|---|---|
| EP | 887640 | 12/1998 |
| EP | 892265 | 1/1999 |

(Continued)

OTHER PUBLICATIONS

Database WPI, Section Ch, Week 199516, Derwent Publications Ltd., London, GB/Class E36, AN 1995-119370, XP002288448 & JP 07 043338 A (Matsushita Denki Sangyo KK), Feb. 14, 1995.

*Primary Examiner*—Binh Q. Tran
(74) *Attorney, Agent, or Firm*—Nixon & Vanderhye P.C.

(57) ABSTRACT

A fault detecting apparatus for a gas concentration sensor is provided. The apparatus includes a storage device and a fault detecting circuit. The storage device stores therein fault detectable conditions in which preselected different types of faults of the gas concentration sensor are allowed to be detected, respectively. The fault detecting circuit works to detect a selected one of the faults stored in said storage device. When one of the fault detectable conditions is encountered during operation of the gas concentration sensor, the fault detecting circuit initiates detection of a corresponding one of the faults based on an output of the gas concentration sensor, thereby enabling the fault detecting circuit to identify the type of one of the faults to be detected correctly.

29 Claims, 13 Drawing Sheets

FOREIGN PATENT DOCUMENTS

| | | |
|---|---|---|
| EP | 0892265 A1 | 1/1999 |
| EP | 1231465 A2 | 8/2002 |
| JP | 11-14589 | 1/1999 |
| JP | 11-37972 | 2/1999 |

* cited by examiner

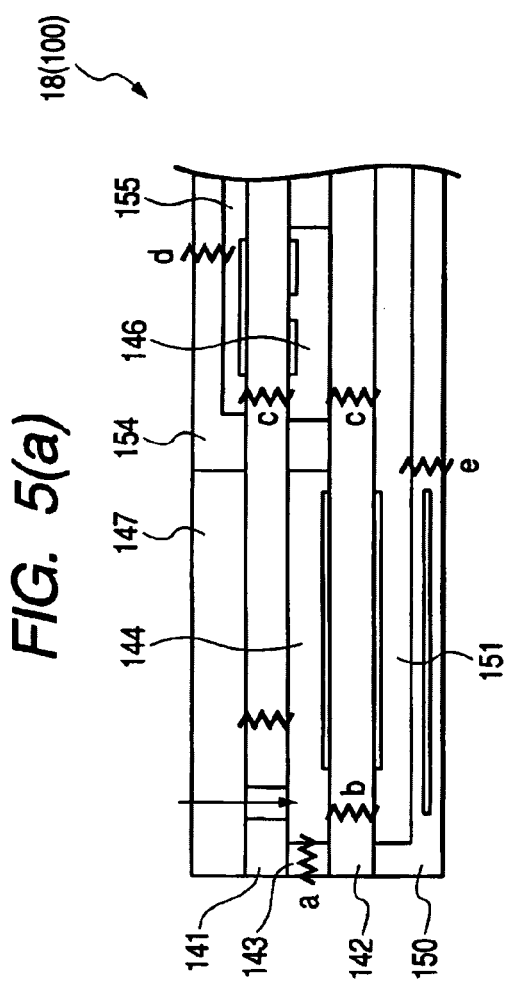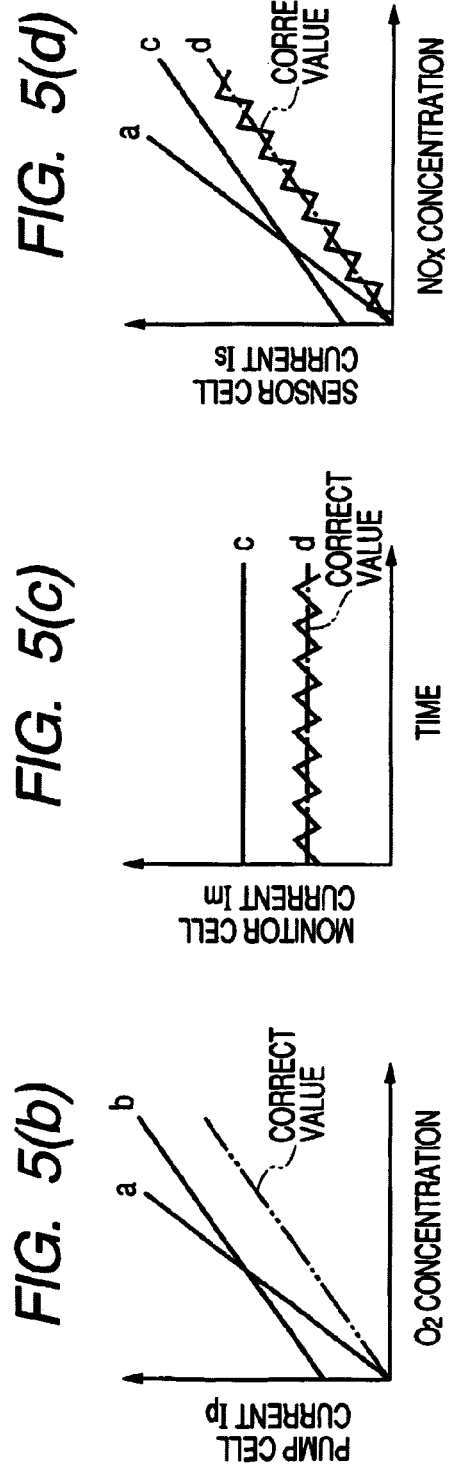

FAULT DETECTING APPARATUS DESIGNED TO DETECT DIFFERENT TYPES OF FAULTS OF GAS SENSOR

BACKGROUND OF THE INVENTION

1. Technical Field of the Invention

The present invention relates generally to a fault detecting apparatus for a gas concentration sensor which is designed to detect and identify different types of faults of the sensor accurately.

2. Background Art

NOx sensors are known which measure the concentration of nitrogen oxides (NOx) contained in exhaust emissions of automotive engines. Such sensors are typically used in an emission control systems for lean burn internal combustion engines equipped with a NOx catalyst absorbing NOx emitted during lean burn of the engine. The NOx sensor is installed downstream of the NOx catalyst. When the quantity of NOx absorbed in the NOx catalyst increases or sulfur emissions contained in the exhaust gas are adhered to the NOx catalyst, thus resulting in decreased ability to absorb the NOx, the emission control system finds such an event through an output of the NOx sensor and enriches an air-fuel ratio of a mixture supplied to the engine to recondition the NOx catalyst.

Japanese patent First Publication No. 11-14589 (equivalent to EP 0887640) teaches a diagnostic system working to diagnose faults in a gas concentration sensor. This system makes such a diagnosis using the fact that the temperature of the gas concentration sensor bears a correlation to an ac resistance (i.e., impedance) thereof. Specifically, when a heater installed in the sensor is energized so as to bring the ac resistance to within a given reference range, but the ac resistance lies out of the reference range, the diagnostic system determines that any fault has occurred in the sensor.

Japanese Patent First Publication No. 11-37972 (equivalent to EP 0892265) also teaches a diagnostic system for a gas concentration sensor equipped with a main pump cell, a first gas chamber, and a second gas chamber. A feedback control system works to control a pumping operation of the main pump cell to adjust a partial pressure of oxygen within the first gas chamber to a level not to decompose NOx gases. If the feedback control system is controlled using a correcting circuit, but it is difficult to bring the concentration of oxygen within the second gas chamber into agreement with a target level, the diagnostic system determines that the gas concentration sensor is malfunctioning for some reason.

The diagnostic systems, as described above, have the drawback in that it is impossible to locate the fault in the sensor. Specifically, diagnostic systems of this type are capable of detecting a failure in operation of the sensor itself, but cannot take action about the failure. For example, it is possible to take action to correct sensor control schemes without replacing the sensor itself in some types of faults, but however, the above diagnostic systems have a difficulty in identifying such an event.

SUMMARY OF THE INVENTION

It is therefore a principal object of the present invention to avoid the disadvantages of the prior art.

It is another object of the present invention to provide a fault detecting system for a gas concentration sensor which is capable of detecting a fault(s) in the sensor and identifying a type thereof.

According to one aspect of the invention, there is provided a fault detecting apparatus for a gas concentration sensor. The gas concentration sensor has a sensor element which includes a solid electrolyte body, a plurality of electrodes affixed to the solid electrolyte body, and a gas chamber to which a gas to be measured is introduced and at least one of the electrode is exposed. The sensor element works to produce an electrical signal between two of the electrodes as a function of the amount of oxygen ions traveling through the solid electrolyte body. The fault detecting apparatus comprises: (a) a storage device which stores therein fault detectable conditions in which preselected different types of faults of the gas concentration sensor are allowed to be detected, respectively; and (b) a fault detecting circuit working to detect a selected one of the faults stored in the storage device. When one of the fault detectable conditions is encountered during operation of the gas concentration sensor, the fault detecting circuit initiates detection of a corresponding one of the faults based on an output of the gas concentration sensor. This enables the apparatus to identify the type of one of the faults to be detected.

In the preferred mode of the invention, when one of the fault detectable conditions in which a concentration of oxygen in the gas is known is encountered, the fault detecting circuit works to initiate detection of a corresponding one of the faults of the gas concentration sensor. Specifically, the output of the gas concentration sensor is usually known in advance when the concentration of oxygen is known. It is, thus, easy to identify the type of the fault.

When one of the fault detectable conditions in which a concentration of oxygen in the gas has a given higher value is encountered, the fault detecting circuit detects a resulting output of the gas concentration sensor. When the resulting output shows a value decreased below a correct one, the fault detecting circuit determines that one of the faults in introducing the gas into the gas chamber has occurred. Specifically, when the concentration of oxygen increases, it will result in an increase in the output of the gas concentration sensor if the gas concentration sensor is operating normally. Therefore, if the output of the gas concentration sensor is lower than a correct one, it is possible to determine that the fault has occurred in introducing the gas into the gas chamber.

When the output of the gas concentration sensor is smaller than a threshold used to determine the fault in introducing the gas into the gas chamber, the fault detecting circuit determines as one of the faults that a wire leading to one of the electrodes of the sensor element has been broken.

When one of the fault detectable conditions in which a concentration of oxygen in the gas has a given higher value is encountered, and a resulting output of the gas concentration sensor is greater than a preselected normal range, the fault detecting circuit determines as one of the faults that a crack is formed in a partition wall defining the gas chamber. Specifically, if the partition wall defining the gas chamber is cracked, it will cause an excess of oxygen gas to enter the gas chamber, thus resulting in a greatly increased output of the sensor. Thus, if such an event is encountered, the partition wall may be determined to have been cracked.

The fault detecting apparatus may be used with an exhaust system of an automotive internal combustion engine. In this case, when one of the fault detectable conditions in which the engine is undergoing a fuel cut is encountered, the fault detecting circuit may initiate the detection of the corresponding one of the faults of the gas concentration sensor. Usually, the concentration of oxygen contained in the exhaust gas during a fuel cut of the engine shows a known value of approximately 20.6%. Therefore, when the fact that the engine is undergoing a fuel cut is found, the fault detecting circuit may identify the above described gas introduction failure, the wire breakage, and the defect in the partition wall.

The gas concentration sensor may also include a reference oxygen gas chamber facing the gas chamber across the solid electrolyte body. In this case, when one of the fault detectable conditions in which a concentration of oxygen in the gas changes to a given lower value is encountered, and a resulting value of the output of the gas concentration sensor is different from one corresponding to the given lower value, the fault detecting circuit determines as one of the faults that a crack is formed in a partition wall defining the reference oxygen gas chamber. Additionally, in a case where an exhaust gas of an automotive internal combustion engine is introduced into the gas chamber, when one of the fault detectable conditions in which a rich air-fuel ratio corresponding exhaust gas is introduced into the gas chamber is encountered, the fault detecting circuit may initiate the above detection. Specifically, if the partition wall exposed to the reference oxygen gas chamber is cracked, it will cause the exhaust gas to enter the reference oxygen gas chamber, so that the reference oxygen gas chamber will be identical in the concentration of oxygen with the gas chamber. The causes the output of the sensor to change to a level indicating a decrease in the concentration of oxygen. Using this fact, a determination may be made whether the partition wall exposed to the reference oxygen gas chamber has been cracked or not.

When one of the fault detectable conditions in which a time when it is unnecessary to measure a concentration of the gas is reached is encountered, the fault detecting circuit increases and decreases a voltage applied across the two of the electrodes of the sensor element to determine a resistance value of the sensor element. When the resistance value is greater than a given value, the fault detecting circuit determines as one of the faults that a failure has occurred in activating the sensor element. Specifically, the voltage applied to the sensor element is changed when the concentration of the gas needs not be measured, thus not disturbing the measurement of the concentration of the gas itself.

When one of the fault detectable conditions in which the output of the gas concentration sensor increases up to near a limit of a current capacity of a driver circuit used to actuate the sensor element during operation of the gas concentration sensor, the fault detecting circuit determines as one of the faults that an electrical short has occurred between the electrodes of the sensor element.

According to the second aspect of the invention, there is provided a fault detecting apparatus for a gas concentration sensor equipped with a sensor element including a first chamber into which a gas to be measured is introduced, a second chamber leading to the first chamber, a first cell which works to pump oxygen into and out of the first chamber selectively to keep a concentration of oxygen at a given level within the first chamber and produces an electrical signal as a function of the concentration of oxygen, and a second cell which works to produce an electrical signal as a function of a concentration of a specified component of the gas flowing from the first chamber into the second chamber. The fault detecting apparatus comprises: (a) a storage device which stores therein fault detectable conditions in which preselected different types of faults of the gas concentration sensor are allowed to be detected, respectively; and (b) a fault detecting circuit working to detect a selected one of the faults stored in the storage device, when one of the fault detectable conditions is encountered during operation of the gas concentration sensor. The fault detecting circuit works to initiate detection of a corresponding one of the faults based on outputs of the first and second cells. This enables the apparatus to identify the type of one of the faults to be detected accurately.

In the preferred mode of the invention, when one of the fault detectable conditions in which the concentration of oxygen in the gas is known is encountered, the fault detecting circuit initiates detection of a corresponding one of the faults of the gas concentration sensor using the output of the first cell. Specifically, the output of the first cell is usually known in advance when the concentration of oxygen is known. It is, thus, easy to identify the type of the fault.

When one of the fault detectable conditions in which the concentration of oxygen in the gas has increased is encountered, the fault detecting circuit monitors a resulting output of the first cell. When the resulting output shows a value smaller than that corresponding to an increase in the concentration of oxygen, the fault detecting circuit determines that one of the faults in introducing the gas into the first chamber has occurred. Specifically, when the concentration of oxygen increases, it will result in an increase in the output of the first cell if the gas concentration sensor is operating normally. Therefore, if the output of the first cell is lower than a correct one, it is possible to determine that the fault has occurred in introducing the gas into the first chamber.

When the output of the first cell is smaller than a threshold used to determine the fault in introducing the gas into the first chamber, the fault detecting circuit determines as one of the faults that a wire leading to an electrode of the first cell has been broken.

When one of the fault detectable conditions in which the concentration of oxygen in the gas has a given higher value is encountered, and a resulting output of the first cell is greater than a preselected normal range, the fault detecting circuit determines as one of the faults that a crack is formed in a partition wall defining the first chamber. Specifically, if the partition wall exposed to the first chamber is cracked, it will cause an excess of oxygen gas to enter the first chamber, thus resulting in a greatly increased output of the first cell. Thus, if such an event is encountered, the partition wall may be determined to have been cracked.

The fault detecting apparatus may be employed in an exhaust system of automotive internal combustion engine. In this case, when one of the fault detectable conditions in which the engine is undergoing a fuel cut is encountered, the fault detecting circuit initiates the detection of the corresponding one of the faults of the gas concentration sensor. Usually, the concentration of oxygen contained in the exhaust gas during a fuel cut of the engine has a known value of approximately 20.6%. Therefore, when the fact that the engine is undergoing a fuel cut is found, the fault detecting circuit may identify the above described gas introduction failure, the wire breakage, and the defect in the partition wall.

The sensor element may also include a reference oxygen gas chamber facing the gas chamber across the first cell. In this case, when one of the fault detectable conditions in which a concentration of oxygen in the gas changes to a given lower value is encountered, and a resulting value of the output of the first cell is different from one corresponding to the given lower value, the fault detecting circuit determines as one of the faults that a crack is formed in a partition wall defining the reference oxygen gas chamber. Additionally, in a case where an exhaust gas of an automotive internal combustion engine is introduced into the first chamber, when one of the fault detectable conditions in which a rich air-fuel ratio corresponding exhaust gas is introduced into the first chamber is encountered, the fault detecting circuit may initiate the above detection. Specifically, if the partition wall exposed to the reference oxygen gas chamber is cracked, it will cause the exhaust gas to enter the reference oxygen gas chamber, so that the reference oxygen gas chamber will be identical in the concentration of oxygen with the first chamber. This causes the output of the sensor to change to a level indicating a decrease in the concentration of oxygen. Using this fact, a determination may be made whether the partition wall exposed to the reference oxygen gas chamber has been cracked or not.

When one of the fault detectable conditions in which a time when it is unnecessary to measure the concentration of the specified component of the gas is reached is encountered, the fault detecting circuit increases and decreases a voltage applied across electrodes of one of the first and second cells to determine a resistance value of the one of the first and second cells. When the resistance value is greater than a given value, the fault detecting circuit determines as one of the faults that a failure has occurred in activating the one of the first and second cells.

When one of the fault detectable conditions in which the concentration of oxygen in the first chamber is kept by the first cell at the given level is encountered, and when the output of the second cell is greater than a given normal range, the fault detecting circuit determines as one of the faults that a crack is formed in a partition wall defining the second chamber.

When one of the fault detectable conditions in which the output of one of the first and second cells increases up to near a limit of a current capacity of a driver circuit used to actuate the one of the first and second cells during operation of the gas concentration sensor is encountered, the fault detecting circuit determines as one of the faults that an electrical short has occurred between electrodes of the one of the first and second cells.

When one of the fault detectable conditions in which a voltage to be applied to the first cell is decreased below that used to measure the concentration of the specified gas component is encountered, and when a resulting value of the output of the second cell is smaller than a given value, the fault detecting circuit determines as one of the faults that a wire leading to an electrode of the second cell is broken.

When one of the fault detectable conditions in which a time when it is unnecessary to measure the concentration of the specified component of the gas is reached is encountered, the fault detecting circuit shifts a voltage applied to the first cell to a lower level to find a voltage level applied to the first cell at which a value of the output of the second cell changes suddenly in relation to a change in the voltage applied to the first cell. When the found voltage level is greater than a given normal level, the fault detecting circuit determines as one of the faults that a failure has occurred in activating the first cell. Specifically, in the gas concentration sensor of this type, the voltage applied to the first cell and the output of the second cell bears a relation, as illustrated in FIG. 4(b). In FIG. 4(b), Vp indicates the voltage applied to the first cell. Is indicates the output of the second cell. As apparent from the drawing, the voltage Vp has an inflection point at which the output Is changes suddenly. If a failure in activating the first cell, it will cause the inflection point to shift to a higher voltage side. Using this fact, the activation failure of the first cell is detected.

The sensor element may also include a third cell which produces an output as a function of a concentration of oxygen within the second chamber. The gas concentration sensor may be designed to control a voltage applied to the first cell. When a selected one of the fault detectable conditions is encountered during operation of the gas concentration sensor, the fault detecting circuit initiates the detection of a corresponding one of the faults based on the output of the third cell.

When one of the fault detectable conditions in which a time when it is unnecessary to measure the concentration of the specified component of the gas is reached is encountered, the fault detecting circuit increases and decreases a voltage applied to the third cell to find a resistance value of the third cell. When the resistance value is greater than a given value, the fault detecting circuit determines as one of the faults that a failure has occurred in activating the third cell.

When one of the fault detectable conditions in which the concentration of oxygen in the first chamber is kept by the first cell at the given level is encountered, and when the output of the third cell is greater than a given normal range, the fault detecting circuit determines as one of the faults that a crack is formed in a partition wall defining the second chamber.

When one of the fault detectable conditions in which the output of the third cell increases up to near a limit of a current capacity of a driver circuit used to actuate the third cell during operation of the gas concentration sensor is encountered, the fault detecting circuit determines as one of the faults that an electrical short has occurred between electrodes of the third cell.

When one of the fault detectable conditions in which a voltage to be applied to the first cell is decreased below that used to measure the concentration of the specified gas component is encountered, and when a resulting value of the output of the third cell is smaller than a given value, the fault detecting circuit determines as one of the faults that a wire leading to an electrode of the third cell is broken.

When one of the fault detectable conditions in which a time when it is unnecessary to measure the concentration of the specified component of the gas is reached is encountered, the fault detecting circuit shifts a voltage applied to the first cell to a lower level to find a voltage level applied to the first cell at which a value of the output of the third cell changes suddenly in relation to a change in the voltage applied to the first cell. When the found voltage level is greater than a given normal level, the fault detecting circuit determines as one of the faults that a failure has occurred in activating the first cell.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 5(a) is a partially sectional view which shows possible cracks to be formed in a sensor element of a NOx sensor;

FIG. 5(b) is a graph which shows relations between a pump cell current and the concentration of $O_2$ if the cracks, as illustrated in FIG. 5(a), have occurred;

FIG. 5(c) is a graph which shows changes in monitor cell current if the cracks, as illustrated in FIG. 5(a), have occurred;

FIG. 5(d) is a graph which shows relations between a sensor cell current and the concentration of NOx if the cracks, as illustrated in FIG. 5(a), have occurred;

DESCRIPTION OF THE PREFERRED EMBODIMENTS

Figure 1:
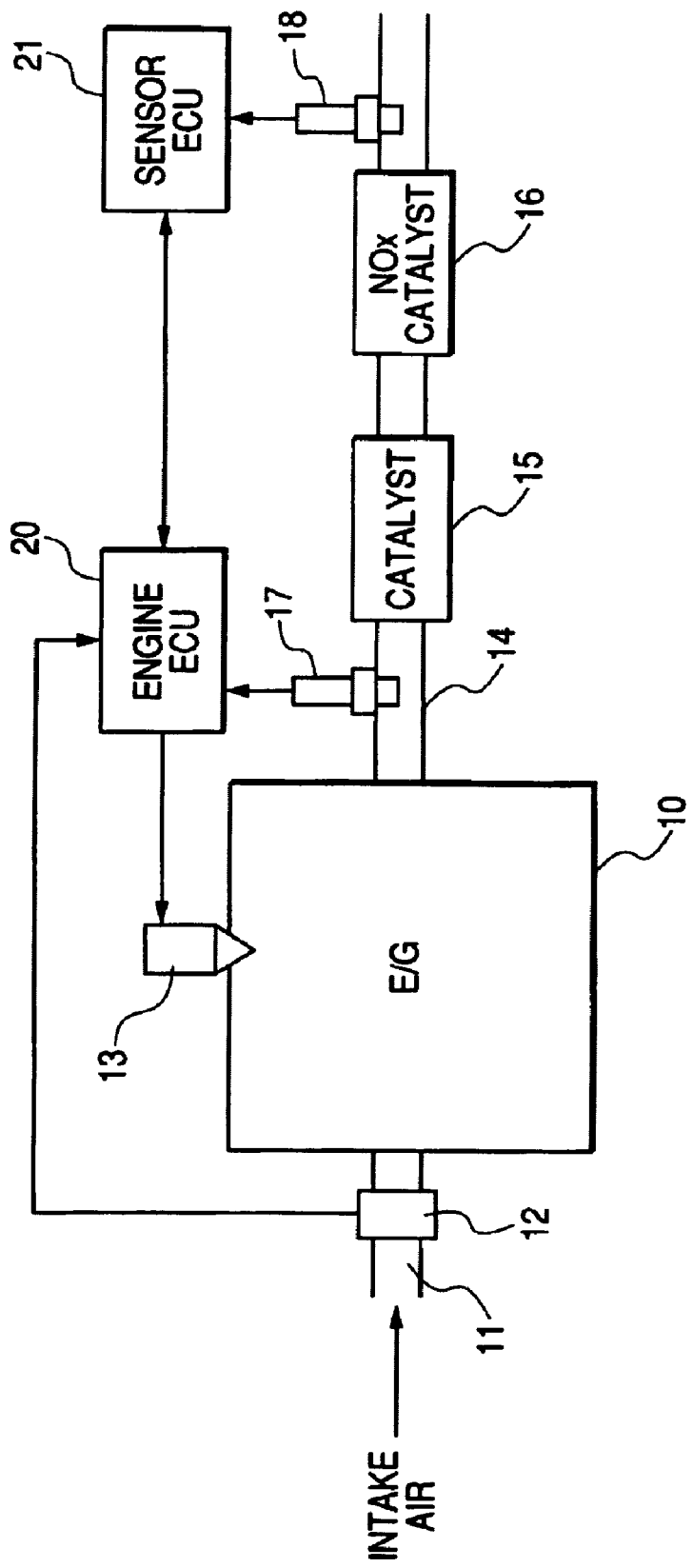
FIG. 1 is a block diagram which shows an emission control system equipped with a fault detecting apparatus according to the invention.

Referring now to the drawings, wherein like numbers refer to like parts in several views, particularly to FIG. 1, there is shown an automotive emission control system designed to control or reduce harmful emissions such as NOx from a gasoline engine of an automotive vehicle. The emission control system is equipped with a NOx sensor, as will be described later in detail, which works to measure the concentration of NOx and a fault detecting apparatus, as will be described later in detail, which works as a diagnostic device to detect a fault(s) in the NOx sensor and identify a type of such a fault.

The emission control system, as clearly shown in the drawing, includes an intake air sensor 12, a fuel injector 13, a three-way catalyst 15, a NOx catalyst 16, an air-fuel ratio (A/F) sensor 17, a NOx sensor 18, an engine electronic control unit (ECU) 20, and a sensor electronic control unit (ECU) 21.

The air is sucked into an internal combustion engine 10 through an intake pipe 11, mixed with fuel sprayed from the fuel injector 13, and injected into a combustion chamber of the engine 10. The intake air sensor 12 measures the quantity of the intake air and provides a signal indicative thereof to the engine ECU 20. An exhaust pipe 14 extends from the engine 10 and has the three-way catalyst 15 and the NOx catalyst 16 installed in series. The three-way catalyst 15 works to clean up or purge three kinds of harmful emissions such as HC, CO, and NOx. The NOx catalyst 16 is implemented by an NOx absorbent reduction catalyst which works to absorb NOx contained in exhaust emissions produced mainly when the air-fuel ratio of a mixture supplied to the engine 10 is on the lean side and reduce the absorbed NOx using rich components of the exhaust emissions (i.e., carbon monoxide CO and hydrocarbon HC) produced when the air-fuel ratio is on the rich side. The A/F sensor 17 is installed upstream of the three-way catalyst 15. The NOx sensor 18 is installed downstream of the NOx catalyst 16.

The engine ECU 20 works to control injection of fuel into and ignition timing of the engine 10 and receive outputs from the intake air sensor 12 and the A/F sensor 17. The engine ECU 20 controls the quantity of fuel sprayed by the fuel injector 3 to bring the air-fuel ratio into a fuel-lean condition in order to improve fuel economy. The sensor ECU 21 is electrically connected to the NOx sensor 18. The sensor ECU 21 works to determine the concentration of NOx contained in the exhaust gas of the engine 10 using an output from the NOx sensor 18 and output a signal indicative thereof to the engine ECU 20.

When NOx emissions contained in the exhaust gas are absorbed in the NOx catalyst 16 during the lean-burn control of the engine 10, it will result in a gradual decrease in NOx-absorbing ability of the NOx catalyst 16, so that some of the NOx emissions not absorbed may be expelled outside the exhaust pipe 14. The NOx sensor 18 measures the concentration of NOx in the exhaust gas flowing downstream of the NOx catalyst 16 and outputs a signal indicative thereof to the engine ECU 20 through the sensor ECU 21. The engine ECU 20 determines whether the NOx-absorbing ability of the NOx catalyst 16 has been lowered or not and perform a recovery operation to recondition the NOx catalyst 16. Specifically, the engine ECU 20 controls the fuel injector 17 and modifies the quantity of fuel injected to the engine 10 so as to bring the air-fuel ratio into a fuel-rich condition temporary, thereby reducing and releasing the NOx emissions from the NOx catalyst 16. Usually, adhesion of sulfur emissions contained in the exhaust gas to the NOx catalyst 16 will also result in a decrease in the NOx-absorbing ability of the NOx catalyst 16, which leads to a greater concern about NOx pollution. This problem is also alleviated by bringing the air-fuel ratio of a mixture supplied to the engine 10 into the fuel-rich condition temporary to have the sulfur emissions react with hydro carbon to burn them off.

Figure 2:
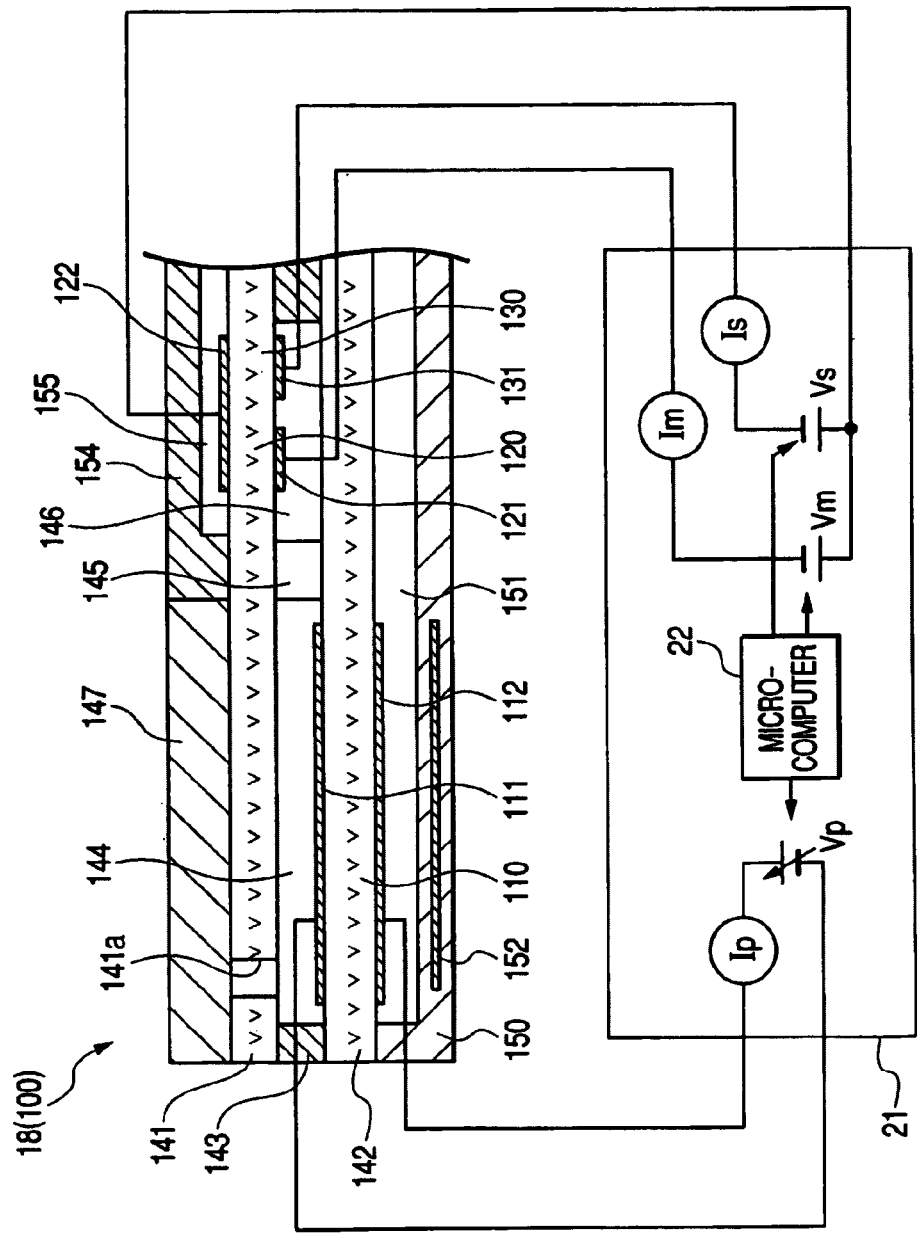
FIG. 2 is a partially sectional view which shows a NOx sensor installed in the emission control system of FIG. 1.

FIG. 2 illustrates an internal structure of a tip portion of the NOx sensor 18 which serves as a sensor element 100. The sensor element 100 is installed in a boy of the NOx sensor 18 and exposed to the exhaust gas flowing through the exhaust pipe 14.

The sensor element 100 is of a three-cell type and made up of a laminate of solid electrolyte layers 141 and 142 made of an oxygen ion-conducting material such as zirconia, a spacer 143, insulating layers 150 and 154, and a porous diffusion layer 147. The solid electrolyte layers 141 and 142 are laid to overlap each other at a given interval through the spacer 143 made of an insulating material such as alumina.

The solid electrolyte layer 141 has formed therein a pinhole 141a (i.e., a gas inlet) through which an exhaust gas (will also be referred to as a measurement gas below) flowing around the NOx sensor 18 are admitted into a first chamber 144. The first chamber 144 communicates with a second chamber 146 through an orifice 145. The porous diffusion layer 147 is affixed to an upper surface of the solid electrolyte layer 141. The porous diffusion layer 147 works to provide the resistance to diffusion of the exhaust gas passing therethrough. The insulating layer 154 defines therein an air passage 155 leading to the atmosphere. The air passage 155 serves as a reference oxygen gas chamber into which an oxygen gas whose concentration is known is introduced.

The solid electrolyte layer 142 has formed therein a pump cell 110. The pump cell 110 works to dissociate or ionize and pump thereinto oxygen molecules ($O_2$) contained the exhaust gas admitted into the first chamber 144 and discharge them to an air passage 151 for measuring the concentration of oxygen ($O_2$) contained in the exhaust gas and also to dissociate or ionize and pump oxygen molecules ($O_2$) within the air passage 151 into the first chamber 144 when the concentration of oxygen within the first chamber 144 is lower than a given low level for keeping the concentration of oxygen within the first chamber 144 at the given low level. The air passage 151, like the air passage 155, serves as a reference oxygen gas chamber. The pump cell 110 has a pair of upper and lower electrodes 111 and 112 disposed on opposed surfaces thereof. The upper electrode 111 is exposed to the first chamber 144 and inactive with respect to NOx, that is, hardly decomposes NOx. Application of voltage Vp across the electrodes 111 and 112 causes the pump cell 110 to perform the above pumping operation.

The solid electrolyte layer 141 has formed therein a monitor cell 120 and a sensor cell 130 facing the second chamber 146. Upon application of the voltage, the monitor cell 120 produces an electric current as a function of the concentration of oxygen within the second chamber 146. The monitor cell 120 may alternatively be designed to be responsive to the oxygen gas flowing from the first chamber 144 to the second chamber 146 to produce an electromotive force as a function of the concentration of oxygen within the second chamber 146. The sensor cell 130 serves to measure the concentration of NOx contained in the exhaust gas having passed through the pump cell 110.

The monitor cell 120 and the sensor cell 130 are disposed close to each other. The monitor cell 120 has a pair of lower and upper electrodes 121 and 122 disposed on opposed surfaces thereof. The upper electrode 122 is exposed to the air passage 155. The lower electrode 121 is exposed to the second chamber 146 and made of a noble metal such as Au—Pt inactive with respect to NOx gas. The sensor cell 130 has a lower electrode 131 and shares the upper electrode 122 with the monitor cell 120. The lower electrode 131 is exposed to the second chamber 146 and made of a noble metal such as Rhodium (Rh) active with respect to NOx gas. The monitor cell 120 and the sensor cell 130 are illustrated as being arrayed adjacent each other in a direction of flow of the measurement gas for the brevity of illustration, but, they are, in practice, disposed in parallel at the same location in the direction of flow of the measurement gas.

The insulating layer 150 is disposed on a lower surface, as viewed in the drawing, of the solid electrolyte layer 142 to define the air passage 151. The insulating layer 150 has embedded therein a heater 152 which is supplied with electric power from a battery installed in the vehicle to heat the whole of the NOx sensor 18 (i.e., the pump cell 110, the monitor cell 120, and the sensor cell 130) up to a given activation temperature. For convenience of explanation, the air passages 151 and 155 will also be referred to as a first and a second air passage below, respectively.

The sensor ECU 21, as shown in FIG. 2, includes a microcomputer 22 working to control an operation of the NOx sensor 18. The microcomputer 22 controls the voltages Vp, Vm, and Vs to be applied across the electrodes 111 and 112 of the pump cell 110, the electrodes 121 and 122 of the monitor cell 120, and the electrodes 131 and 122 of the sensor cell 130, respectively, and receives a pump cell current Ip, a monitor cell current Im, and a sensor cell current Is produced in the pump cell 110, the monitor cell 120, and the sensor cell 130, respectively.

The exhaust gas enters the first chamber 144 through the porous diffusion layer 147 and the pinhole 141a and passes through the pump cell 110. When the voltage Vp is applied across the electrodes 111 and 112 of the pump cell 110, the pump cell 110 works to ionize and pump oxygen molecules into or out of the first chamber 144 selectively based on the concentration of oxygen ($O_2$) within the first chamber 144. Since the upper electrode 111 of the pump cell 110 is, as described above, made of a metal inactive with NOx, when the concentration of oxygen within the first chamber 144 is higher than a given lower level, only $O_2$ molecules within the first chamber 144 are ionized by the pump cell 110 without decomposing NOx, which are, in turn, discharged to the air passage 151, so that the concentration of oxygen within the first chamber 144 is kept at the given lower level. This causes the pump cell current Ip to be produced in the pump cell 110 as a function of the oxygen content of the exhaust gas. EP0 987 546 A2, assigned to the same assignee as that of this application, teaches control of an operation of this type of gas sensor, disclosure of which is incorporated herein by reference.

The oxygen molecules in the exhaust gas are usually not dissociated by the pump cell 110 completely, so that residual oxygen molecules flow into the second chamber 146 and reach the monitor cell 120. The application of the voltage Vm to the monitor cell 120 through the electrodes 121 and 122 causes the monitor cell current Im to be produced as a function of the concentration of the residual oxygen. The application of the voltage Vs to the sensor cell 130 through the electrodes 131 and 122 causes NOx molecules contained in the exhaust gasses to be decomposed or reduced, so that oxygen ions are produced and discharged from the electrode 122 to the air passage 155, thereby causing the sensor cell current Is to flow through the sensor cell 130 as a function of the concentration of NOx contained in the exhaust gas.

Figure 3A:
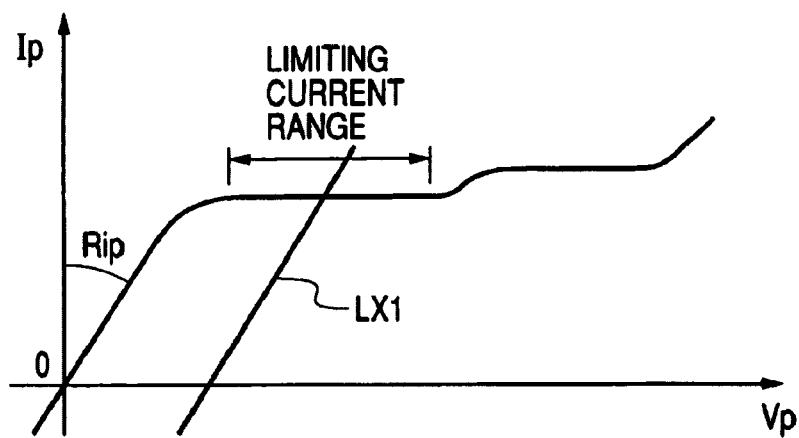
FIG. 3(a) is a graph which shows a relation between a current output of a pump cell and a value of voltage to be applied to the pump cell and a target applying voltage line used to determine a target value of voltage to be applied to the pump cell.
Figure 3B:
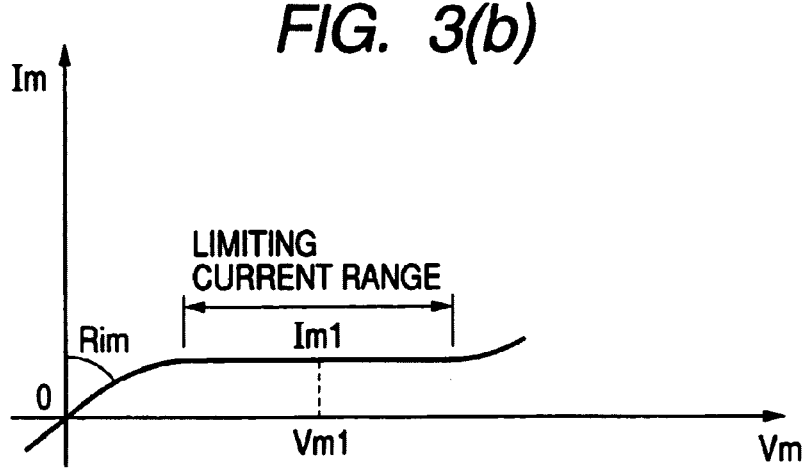
FIG. 3(b) is a graph which shows a relation between a current output of a monitor cell and a value of voltage applied to the monitor cell.
Figure 3C:
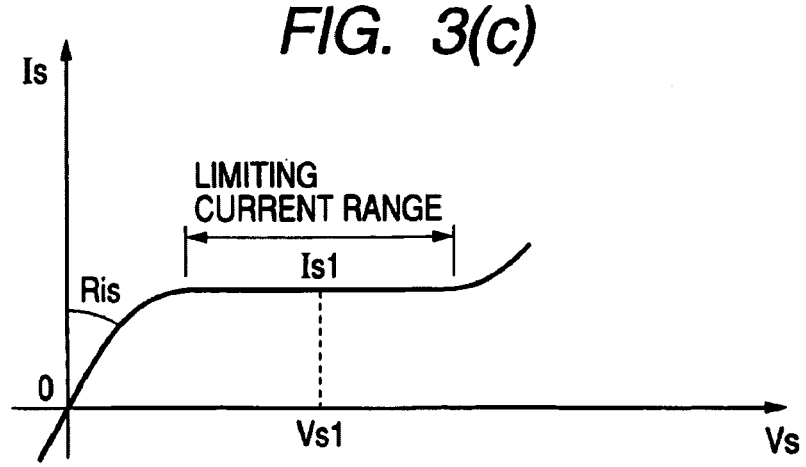
FIG. 3(c) is a graph which shows a relation between a current output of a sensor cell and a value of voltage applied to the sensor cell.

FIGS. 3(a), 3(b), and 3(c) show examples of V-I relations between the voltages Vp, Vm, and Vs applied to the pump cell 110, the monitor cell 120, and the sensor cell 130 and the pump cell current Ip, the monitor cell current Im, and the sensor cell current Is, respectively. Note that FIGS. 3(a) to 3(c) illustrate sensor output characteristics when the concentration of $O_2$ and NOx are constant.

The pump cell 110 works to produce a limiting current as a function of the concentration of oxygen ($O_2$) within the first chamber 144. A straight segment of a curve, as shown in FIG. 3(a), inclined slightly upward with respect to a V-axis (i.e., abscissa axis) indicates a limiting current range in which the limiting current is produced by the pump cell 110. The limiting current range is shifted to the positive side of voltage Vp applied to the pump cell 110 as the concentration of oxygen increases. This characteristic has a resistance-dependent range defined by a segment of the curve extending upward at an inclination substantially depending upon an impedance Rip of the pump cell 110 (i.e., the solid electrolyte plate 142).

The microcomputer 22 stores therein a V-I map such as the one of FIG. 3(*a*) and monitors the pump cell current Ip to determine the voltage Vp to be applied to the pump cell 110 by look-up using the V-I map. The V-I map has a target applying voltage line LX1 and is used in determining the pump cell-applied voltage Vp along the line LX1. The upper pump cell electrode 111 of the pump cell 110 exposed to the first chamber 144 is, as described above, made of material inactive with NOx, so that NOx molecules in the exhaust gas are hardly decomposed, but if the voltage applied to the pump cell 110 exceeds a certain upper limit, it will cause the NOx molecules to be decomposed, thereby producing an error of the pump cell current Ip (i.e., the limiting current) outputted from the pump cell 110. In practice, the target applying voltage line LX1 is so defined as to keep the concentration of oxygen ($O_2$) within the first chamber 144 at a lower level. For instance, the target applying voltage line LX1 is so selected that a small quantity of $O_2$ (e.g., several ppm to several tens ppm) remains in the first chamber 144.

The monitor cell 120, like the pump cell 110, works to produce a limiting current as a function of the concentration of oxygen ($O_2$) within the second chamber 146. The application of a given voltage Vm1, as shown in FIG. 3(*b*), to the monitor cell 120 causes a current Im1 to be produced. When the concentration of oxygen within the second chamber 146 is also kept at a lower level, e.g., several ppm to several tens ppm, by the activity of the pump cell 110, the monitor cell 120 produces a monitor cell current Im of the order of several tens nA.

The sensor cell 130 works to produce a limiting current as a function of the concentration of NOx. Specifically, the sensor cell 130 provides an output as a function of the concentration of NOx contained in the exhaust gas within the second chamber 146. The application of a given voltage Vs1, as shown in FIG. 3(*c*), to the sensor cell 130 causes a current Is1 to be produced.

Figure 4A:
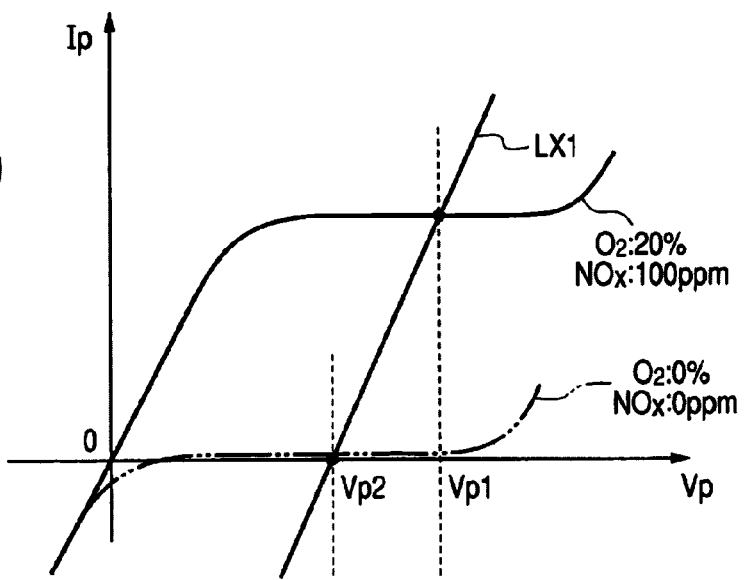
FIG. 4(a) is a graph which shows relations between a current output of a pump cell and a value of voltage applied to the pump cell in different gas atmospheric conditions.
Figure 4B:
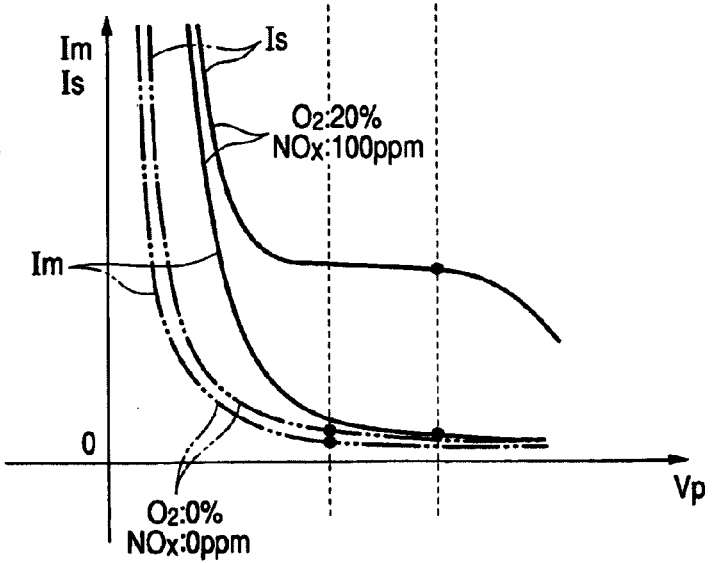
FIG. 4(b) is a graph which shows changes in outputs of a monitor cell and a sensor cell with a change in voltage applied to a pump cell in different gas atmospheric conditions.

FIG. 4(*a*) shows an example of output characteristics (i.e., the pump cell current Ip) of the pump cell 110 in terms of the pump cell-applied voltage Vp. FIG. 4(*b*) shows an example of output characteristics (i.e., the monitor cell current Im and the sensor cell Is) of the monitor cell 120 and the sensor cell 130 in terms of the pump cell-applied voltage Vp. In each of FIGS. 4(*a*) and 4(*b*), a solid curve illustrates for the case where the oxygen concentration is 20%, and the NOx concentration is 100 ppm. A two-dot chain curve illustrates for the case where the oxygen concentration is 0%, and the NOx concentration is 0 ppm. To the monitor cell 120 and the sensor cell 130, the voltages Vm1 and Vs1 are applied, respectively.

As shown in FIG. 4(*a*), when the oxygen concentration is 20%, the microcomputer 22 applies the voltage Vp1 to the pump cell 110. When the oxygen concentration is 0%, the microcomputer 22 applies the voltage Vp2 to the pump cell 110. As can be seen from FIG. 4(*b*), when the pump cell-applied voltage Vp is in a lower level range, the monitor cell current Im changes greatly, but is converged on a constant level when the pump cell-applied voltage Vp rises. Specifically, when the pump cell-applied voltage Vp is low and lies within a resistance-dependent range, the pup cell current Ip is small, meaning that the quantity of oxygen staying within the first chamber 144 is great. In the limiting current range of the pump cell 110, the pump cell current Ip is kept almost constant, meaning that the quantity of oxygen staying within the first chamber 144 is kept almost constant.

The monitor cell current Im, therefore, changes along curves, as illustrated in FIG. 4(*b*), as a function of the pump cell-applied voltage Vp. When the pump cell-applied voltage Vp is controlled within a given range (e.g., 0.3 to 0.6V), the monitor cell current Im has a constant lower level (e.g., several tens nA) regardless of the concentration of oxygen and NOx contained in the exhaust gas.

The output characteristics of the sensor cell 120, as shown in FIG. 4(*b*), has a flat range within which the sensor cell current Is is in a constant level regardless of a change in the pump cell-applied voltage Vp. Therefore, accurate measurement of the concentration of NOx in the exhaust gas is achieved by controlling the pump cell-applied voltage Vp within a range of Vp1 to Vp2.

If a failure in operation of the NOx sensor 18 arises from deterioration or breakage of the NOx sensor 18, it will result in an error in determining the concentration of NOx in the exhaust gas, which leads to an error in the emission control of the engine. It is, thus, necessary to monitor occurrence of such a failure to switch an operation mode of the emission control system to a failsafe mode in which the air-fuel ratio is enriched based on a travel distance of the vehicle or to install an on-board diagnostic (OBD) system in the vehicle which informs a vehicle operator of the failure of the NOx sensor and urges the vehicle operator to replace it. To this end, a fault detection logic is constructed in the microcomputer 22 to monitor and detect faults in the NOx sensor 18.

The detection of faults in the NOx sensor 18, as performed in the microcomputer 22, will be described below in terms of the types of faults and resulting behavior of the NOx sensor 18.

1 Deterioration of Whole of Sensor 1.1 Clogging of Gas Inlet 141*a* and Porous Diffusion Layer 147.

If the gas inlet 141*a* and/or the porous diffusion layer 147 are clogged with solid particles contained in the exhaust gas, it will result in a decrease in the quantity of exhaust gas per unit time introduced into the first chamber 144 (i.e., a flow rate of the exhaust gas entering the first chamber 144). This causes the pump cell current Ip produced by the pump cell 110 to be decreased against the degree of concentration of oxygen in the exhaust gas. In other words, the pump cell current Ip shows a value smaller than a correct one, thus resulting in lowered sensitivity of the NOx sensor 18 to the oxygen gas. When the supply of fuel to the engine 10 is cut, the concentration of oxygen in the exhaust gas (about 20.6%) is constant and known, thus enabling a correct value of the pump cell current Ip to be projected mathematically. A determination of whether the gas inlet 141*a* or the porous diffusion layer 147 has been clogged or not may, therefore, be achieved by monitoring whether the pump cell current Ip is smaller than a normal range or not. Although not illustrated in FIG. 2, the sensor element 100 is, in practice, surrounded by a protective cover with many gas holes. Clogging of the gas holes causes the NOx sensor 18 to exhibit substantially the same behavior as described above. When such an event occurs, it may, therefore, be detected by monitoring the pump cell current Ip in the same manner as described above.

1.2 Crack in Partition of Sensor Element 100.

If a partition(s) exposed to the first and second chambers 144 and 146 or the air passages 151 and 155 is cracked, the behavior of the NOx sensor 18 changes depending upon the location of the crack. A thermal impact on the NOx sensor 18 may be considered as one of causes of such a crack. FIG.

5(a) illustrates possible cracks a, b, c, d, and e in the sensor element 100 of the NOx sensor 18. FIGS. 5(b), 5(c), and 5(d) represent changes in an output of the NOx sensor 18 resulting from the respective cracks as illustrated in FIG. 5(a). In FIGS. 5(b), 5(c), and 5(d), two-dot chain lines represent correct values of the pump cell current Ip, the monitor cell current Im, and the sensor cell current Is before occurrence of the cracks, respectively.

If a crack(s) is, as indicated by a, formed in the solid electrolyte layer 141 or the spacer 143 facing the first chamber 144, it causes the exhaust gas to flow into the first chamber 144 through the crack, so that the pump cell current Ip per unit concentration of oxygen, as shown in FIG. 5(b), increases. Accordingly, the pump cell current Ip when the engine 10 is undergoing a fuel cut will be greater than that before occurrence of the crack. The crack may, thus, be determined to have occurred by finding such an increase in the pump cell current Ip during the fuel cut. Additionally, the sensor cell current Is per unit concentration of NOx, as shown in FIG. 5(d), also increases. The detection of the crack may alternatively be achieved by monitoring such an increase in the sensor cell current Is.

If a crack(s) is, as indicated by b, formed in the solid electrolyte layer 142 facing the first chamber 144 and the air passage 151, it causes the air to flow into the first chamber 144 through the crack, so that the pump cell current Ip, as shown in FIG. 5(b), increases as a whole, that is, it has an offset from the correct value. Accordingly, the pump cell current Ip when the engine 10 is undergoing a fuel cut will be greater than that before occurrence of the crack by a constant degree. The crack may, thus, be determined to have occurred when such an increase in the pump cell current Ip is found during the fuel cut.

If a crack(s) is, as indicated by c, formed in the solid electrolyte layer 141 or 142 facing the second chamber 146, it causes the air flow into the second chamber 146 through the crack, so that the monitor cell current Im and the sensor cell current Is, as shown in FIGS. 5(c) and 5(d), each increase as a whole, that is, they have offsets from the correct values thereof. When the pump cell-applied voltage Vp is kept within a given range (e.g., 0.3V to 0.6V), the monitor cell current Im, as described above in FIG. 4(b), will be low in level (e.g., several tens nA) regardless of the concentration of oxygen and NOx in the exhaust gas. The detection of such a crack may, thus, be achieved by monitoring the monitor cell current Im in such a condition.

If a crack(s) is, as indicated by d, formed in the insulating layer 154 exposed to the exhaust gas and the air in the second air passage 155, it causes the exhaust gas to flow into the second air passage 155, so that it mixes with the air. This, as shown in FIGS. 5(c) and 5(d), results in instability or oscillation of the monitor cell current Im and the sensor cell current Is. The detection of such a crack may be achieved by keeping the concentration of oxygen staying in the second chamber 146 constant and monitoring whether a change or amplitude of the monitor cell current Im has exceeded a given level or not.

If a crack(s) is, as indicated by e, formed in the insulating layer 150 exposed to the exhaust gas and the air in the first air passage 151, it causes the exhaust gas to flow into the first air passage 151, so that it mixes with the air. This will cause the first air passage 151 to be almost identical in the concentration of oxygen with the first chamber 144. In this case, even when a rich gas (i.e., an exhaust gas whose concentration of oxygen is lower than usual) is introduced into the first chamber 144, the pump cell current Ip does not change to a rich side. The crack may, thus, be determined to have occurred when such an event is found.

2 Fault in Each Cell 2.1 Fault in the Pump Cell 110.

As faults in the pump cell 110, breaking of wires leading to the electrodes 111 and 112, an electrical short between the electrodes 111 and 112, and a failure in activating the pump cell 110 may be posed.

If the wire breakage occurs, the pump cell current Ip is not produced between the electrodes 111 and 112. When the engine 10 is subjected to a fuel cut, the pump cell current Ip, as described above, shows a known value. Such wire breakage may, thus, be determined to have occurred when the pump cell current Ip has not exceeded a given threshold when the engine is undergoing a fuel cut. If the short is taken place, it will cause the pump cell current Ip to increase up to a limit of a current capacity of a drive circuit for the pump cell 110. Such a short may, therefore, be determined to have occurred when the pump cell current Ip increases over a predetermined normal range. Additionally, if the electrode 111 or 112 of the pump cell 110 peels off the solid electrolyte layer 142, thereby resulting in a failure in activating the pump cell 110, the resistance Rip, as shown in FIG. 3(a), between the electrode 111 or 112 and the solid electrolyte layer 142 increases, so that an inclination of a segment of the curve within the resistance-dependent range decreases. The detection of such an activation failure in the pump cell 110 may, thus, be achieved by monitoring the resistance Rip.

2.2 Fault in the Monitor Cell 120.

As faults in the monitor cell 120, like the pump cell 110, breaking of wires leading to the electrodes 121 and 122, an electrical short between the electrodes 121 and 122, a failure in activating the monitor cell 120 may be posed.

If the wire breakage occurs, the monitor cell current Im is not produced between the electrodes 121 and 122 regardless of the concentration of oxygen within the second chamber 146. Such wire breakage may, thus, be determined to have occurred by keeping the pump cell-applied voltage Vp lower than the limiting current range (e.g., at 0.1V to 0.2V), thereby resulting in an increased amount of oxygen staying within the second chamber 146 and fining the monitor cell current Im that is lower than a given value. If the short is taken place, it will cause the monitor cell current Im to increase over a value indicating the concentration of oxygen within the second chamber 146. Such a short may, thus, be determined to have occurred when the monitor cell current Im increases over a predetermined normal range. Additionally, if the electrode 121 or 122 of the monitor cell 120 is separated from the solid electrolyte layer 141, thereby resulting in a failure in activating the monitor cell 120, the resistance Rim, as shown in FIG. 3(b), between the electrode 121 or 122 and the solid electrolyte layer 141 increases, so that an inclination of a segment of the curve within the resistance-dependent range decreases. The detection of such an activation failure of the monitor cell 130 may, thus, be achieved by monitoring the resistance Rim.

2.3 Fault in the Sensor Cell 130.

As faults in the sensor cell 130, like the pump cell 110, breaking of wires leading to the electrodes 131 and 122, an electrical short between the electrodes 131 and 122, and a failure in activating the sensor cell 130 may be posed.

If the wire breakage occurs, the sensor cell current Is is not produced between the electrodes 131 and 122 regardless of the concentration of oxygen within the second chamber 146. Such wire breakage may, thus, be determined to have occurred by keeping the pump cell-applied voltage Vp lower than the limiting current range (e.g., at 0.1V to 0.2V), thereby resulting in an increased amount of oxygen staying within the second chamber 146 and fining the sensor cell current Is that is lower than a given value. If the short is taken place, it will cause the sensor cell current Is to increase over a value indicating the concentration of oxygen within the second chamber 146. Such a short may, thus, be determined to have occurred when the sensor cell current Is increases over a predetermined normal range. If the electrode 131 or 122 of the sensor cell 130 is separated from the solid electrolyte layer 141, thereby resulting in a failure in activating the sensor cell 130, the resistance Ris, as shown in FIG. 3(c), between the electrode 131 or 122 and the solid electrolyte layer 141 increases, so that an inclination of a segment of the curve within the resistance-dependent range decreases. The detection of such an activation failure in the sensor cell 130 may, thus, be achieved by monitoring the resistance Ris.

As apparent from the above discussion, the sensor ECU 21 works to identify various types of faults in the NOx sensor 18 by detecting such faults when the above described respective fault detectable conditions are met. The sensor ECU 21 is designed to detect the above faults in four fault detecting modes as discussed below.

The first fault detecting mode is entered when the fuel is being supplied to the engine 10. In this fuel supply mode, the sensor ECU 21 monitors an output of the NOx sensor 18 to detect faults thereof. The second fault detecting mode is entered when the engine 10 is undergoing a fuel cut. In this fuel cut mode, the sensor ECU 21 detects faults in the NOx sensor 18 using the fact that the exhaust gas of the engine 10 has a known constant concentration of oxygen during the fuel cut. The third fault detecting mode is entered when a fuel-rich gas (i.e., an exhaust gas whose concentration of oxygen is low) is being introduced into the NOx sensor 18. The sensor ECU 21 detects faults in the NOx sensor 18 using known values of the pump cell current Ip corresponding to degrees of richness of the gas. The fourth fault detecting mode is entered when it is unnecessary to measure the concentration of NOx. The sensor ECU 21 works to detect faults in the NOx sensor 18 using the dc resistances of the cell 110, 120, and 130, as described above. The fourth fault detecting mode may be performed when it is unnecessary to monitor the ability of the NOx catalyst 16 to absorb NOx in the exhaust gas, e.g., within 30 minutes after the NOx catalyst 16 is reconditioned.

The first to fourth fault detecting modes will be described below in detail.

In the first fault detecting mode which is to be entered when the fuel is being supplied to the engine 10, the sensor ECU 21 detects faults in the NOx sensor 8 and identify types of the faults when the NOx sensor 18 produces an improper output. The sensor ECU 21 monitors the electrode-to-electrode shorts in the cells 110, 120, and 130, the crack in the solid electrolyte layer 141 or 142, as indicated by c in FIG. 5(a), leading to the second chamber 146, and the crack in the insulating layer 154 leading to the second air passage 155, as indicated by d in FIG. 5(a).

Specifically, when the pump cell current Ip is greater than a preselected value Ipa (e.g., 5 mA) lying outside a normal pump cell current range, the sensor ECU 21 determines an electrical short to have occurred between the electrodes 111 and 112 of the pump cell 110. When the monitor cell current Im is greater than a preselected value Ima (e.g., 5 μA) lying outside a normal monitor cell current range, the sensor ECU 21 determines an electrical short to have occurred between the electrodes 121 and 122 of the monitor cell 120. Similarly, when the sensor cell current Is is greater than a preselected value Is a (e.g., 5 μA) lying outside a normal sensor cell current range, the sensor ECU 21 determines an electrical short to have occurred between the electrodes 131 and 122 of the sensor cell 130. Further, when the shorts are not taken place, and the monitor cell current Im is greater than a given value Imb (e.g., 1 μA) in a condition where the concentration of oxygen is kept by the pump cell 110 at a given low level, the sensor ECU 21 determines a crack(s) leading to the second chamber 146 to have occurred. Moreover, when the amplitude of the monitor cell current Im is greater than a given value Imc (e.g., 0.5 μA), the sensor ECU 21 determines a crack(s) leading to the second air passage 155 to have occurred.

In the second fault detecting mode which is to be entered when the engine 10 is undergoing a fuel cut, the sensor ECU 21 detects faults in the NOx sensor 18 and identifies types of the faults when the NOx sensor 18 produces an improper output. The sensor ECU 21 monitors the clogging of the gas inlet 141a and/or the porous diffusion layer 147, the crack, as indicated by a in FIG. 5(a), in the solid electrolyte layer 141 or the spacer 142 leading to the first chamber 144 and the exhaust gas flowing outside the sensor element 100, the crack, as indicated by b in FIG. 5(a), in the solid electrolyte layer 142 leading to the first chamber 144 and the air passage 151, and the breakage of wires leading to the electrodes 111 and 112 of the pump cell 110.

Figure 6:
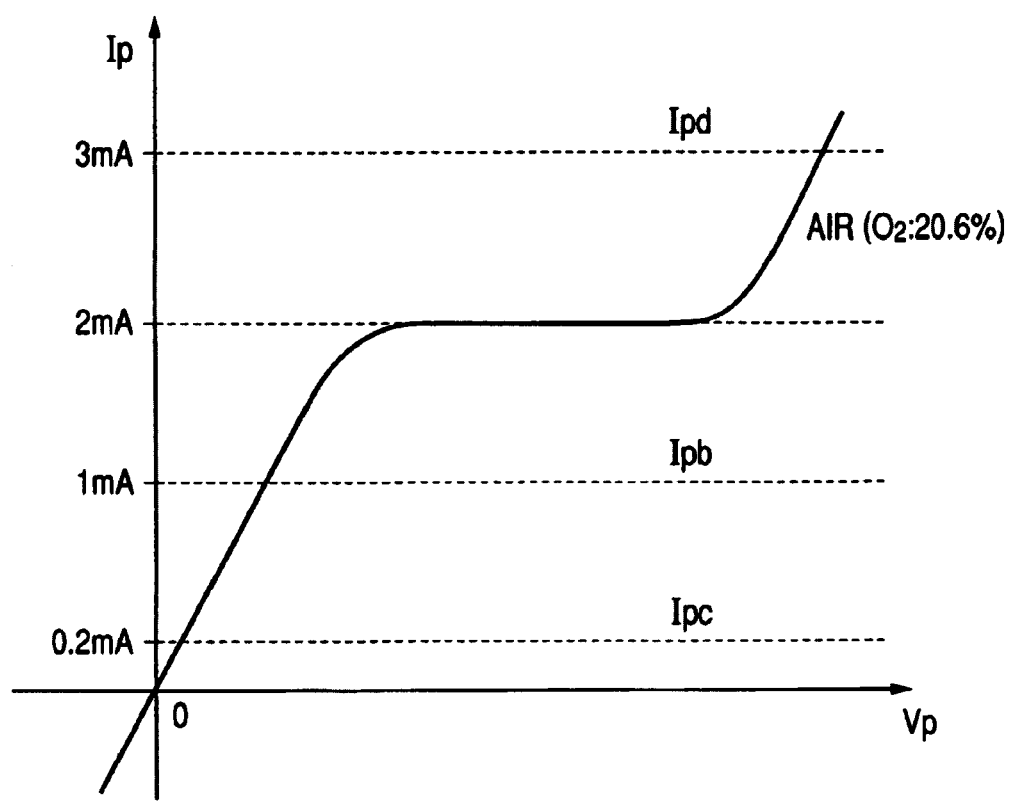
FIG. 6 is a graph which shows a relation between a pump cell current and voltage applied to a pump cell when an engine is undergoing a fuel cut.

Referring to FIG. 6, when the engine 10 is undergoing a fuel cut, the air whose concentration of oxygen is approximately 20% is introduced into the first chamber 144, and the pump cell current Ip of, for example, 2 mA, is produced. When the pump cell current Ip is lower than a given value Ipb of, for example, 1 mA, the sensor ECU 21 determines the gas inlet 141a and/or the porous diffusion layer 147 to have been clogged. When the pump cell current Ip is further lower than a given value Ipc of, for example, 0.2 mA that is smaller than the value Ipb, the sensor ECU 21 determines the wires leading to the electrodes 111 and 112 of the pump cell 110 to be disconnected. When the pump cell current Ip is greater than a given value Ipd of, for example, 3 mA, the sensor ECU 21 determines the crack, as indicated either by a or b in FIG. 5(a), to have been formed in the solid electrolyte layer 141, the spacer 143, or the solid electrolyte layer 142. If the crack, as indicated by a, occurs in the solid electrolyte layer 141 or the spacer 143 to establish communication between outside the sensor element 100 and the first chamber 144, it will, as described above, cause the sensor cell current Is to also increase more than usual. The sensor ECU 21 may also monitor such an event to determine which of the cracks a and b has been formed.

In the third fault detecting mode which is to be entered when a rich gas is being introduced into the NOx sensor 18, the sensor ECU 21 detects faults in the NOx and determines types of the faults when an output of the NOx sensor 18 is improper as indicating the concentration of oxygen contained in a fuel-rich exhaust gas. The sensor ECU 21 works to monitor the crack, as indicated by e in FIG. 5(a), in the insulating layer 150 which communicates between the air passage 151 and outside the sensor element 100. For instance, when the air-fuel ratio is 13, the pump cell 110 usually produces a pump cell current Ip of approximately −0.5 mA. The sensor ECU 21 may determine the above crack to have occurred when the air-fuel ratio is 13, but the pump cell current Ip is −0.3 mA or more.

In the fourth fault detecting mode which is to be entered when it is unnecessary to measure the concentration of NOx, the sensor ECU 21 changes voltages applied to the pump cell 110, the monitor cell 120, and the sensor cell 130 instantaneously and monitors resulting outputs thereof to detect faults in the NOx sensor 18. The sensor ECU 21 works to monitor the breakage of wires leading to the electrodes 121 and 122 of the monitor cell 120 and to the electrodes 131 and 122 of the sensor cell 130, and the failure in activating the pump cell 110, the monitor cell 120, and the sensor cell 130.

Specifically, the sensor ECU 21 applies the voltage Vp which is lower than a usual voltage range to the pump cell 110 to increase the quantity of oxygen within the second chamber 146. If the monitor cell current Im is smaller than a given value Imd of, for example, 1 μA, the sensor ECU 21 determines the wires leading to the electrodes 121 and 122 of the monitor cell 120 to have been disconnected. Similarly, if the sensor cell current Is is smaller than a given value Isd of, for example, 1 μA, the sensor ECU 21 determines the wires leading to the electrodes 131 and 122 of the sensor cell 130 to have been disconnected. The sensor ECU 21 shifts the pump cell-applied voltage Vp to within a resistance-dependent range of the pump cell 110 that is, as can be seen in FIG. 3(*a*), lower than the limiting current range to determine the dc resistance Rip of the pump cell 110. If the dc resistance Rip is greater than or equal to a reference value Ripref of, for example, 120Ω, the sensor ECU 21 determines a failure to have occurred in activating the pump cell 110. Determinations of occurrence of such activation failures in the monitor cell 120 and the sensor cell 130 may be achieved in the same manner as described above.

Figure 7:
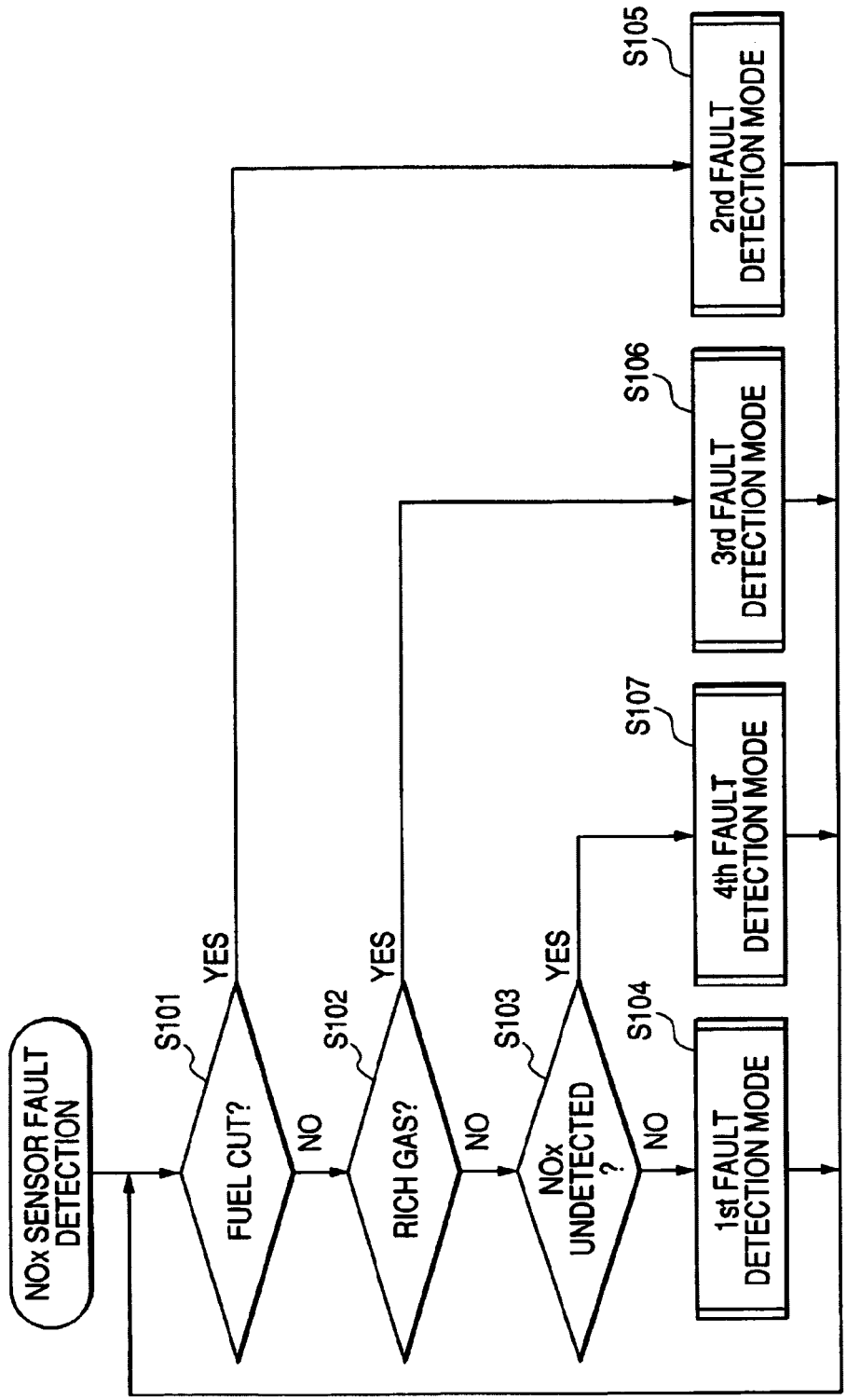
FIG. 7 is a flowchart of a main program executed by a sensor ECU to detect various types of faults in a NOx sensor.
Figure 8:
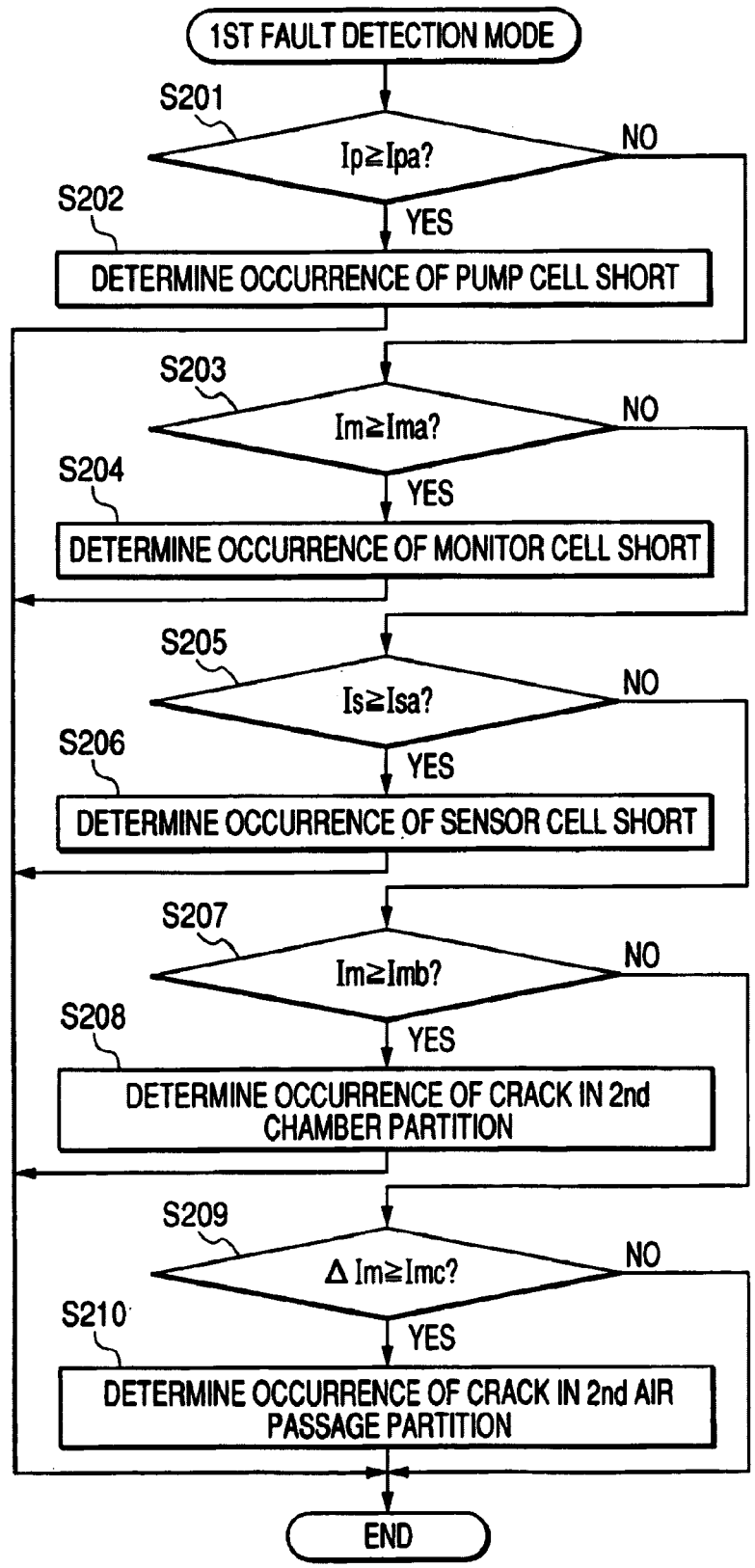
FIG. 8 is a flowchart of a sub-program executed to diagnose faults in a NOx sensor when fuel is being supplied to an engine.
Figure 9:
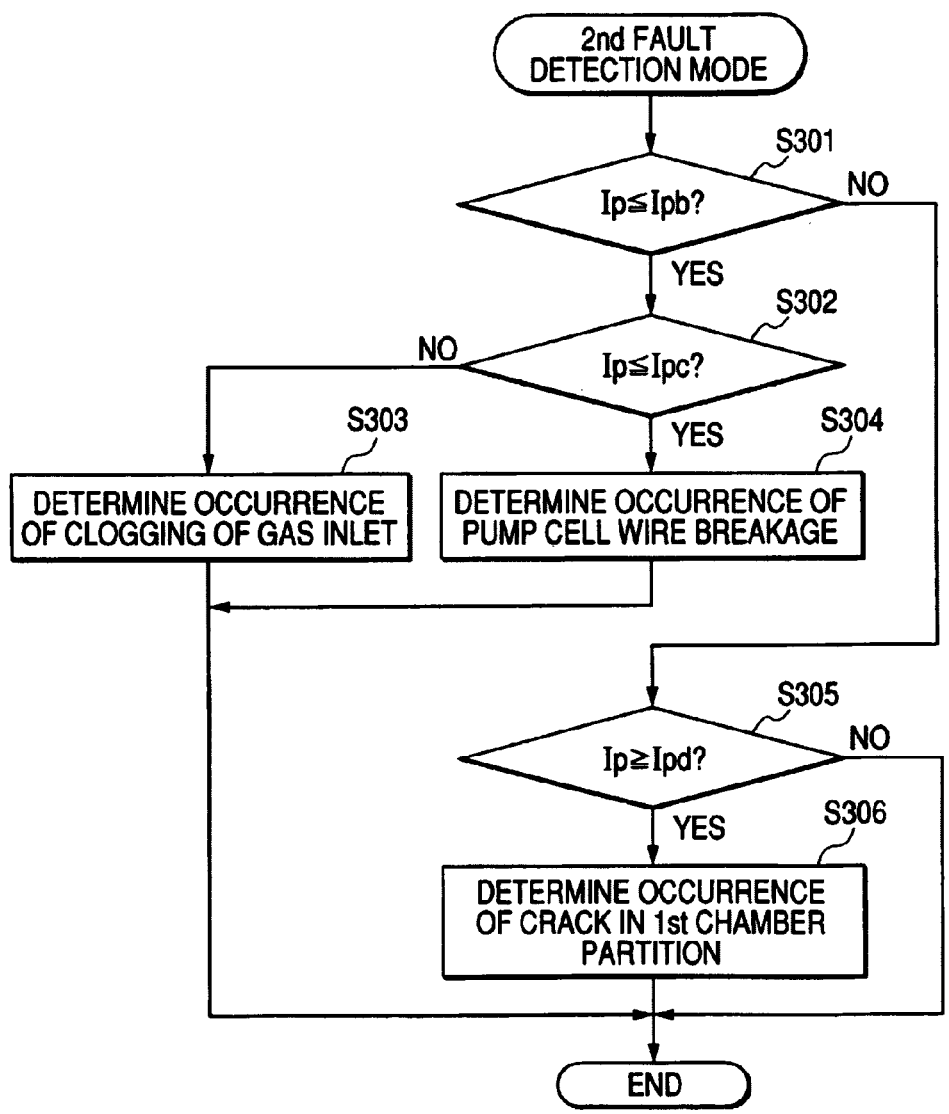
FIG. 9 is a flowchart of a sub-program executed to diagnose faults in a NOx sensor when a supply of fuel to an engine is cut.
Figure 10:
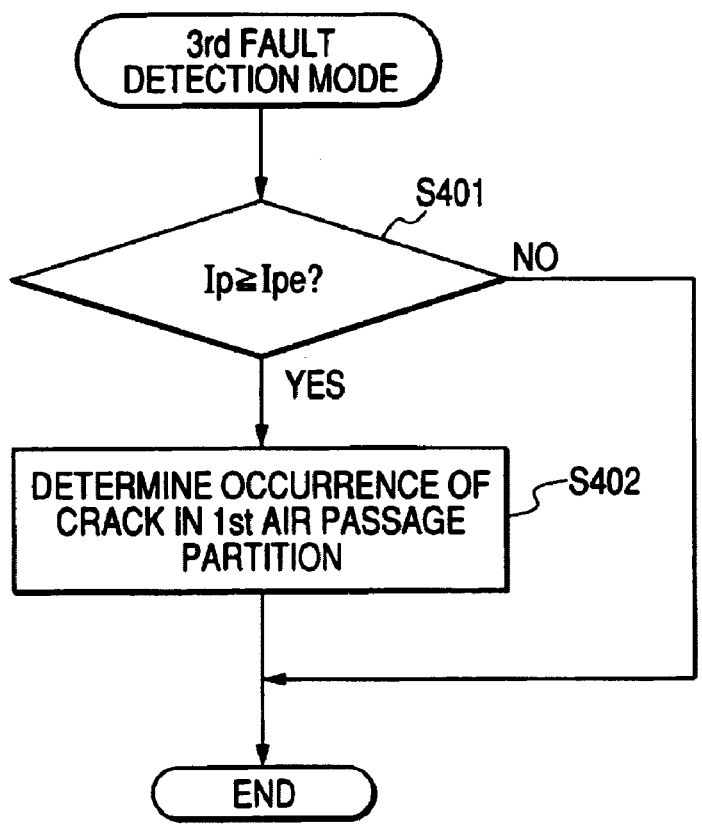
FIG. 10 is a flowchart of a sub-program executed to diagnose faults in a NOx sensor when a rich air-fuel ratio corresponding exhaust gas is introduced into the NOx sensor.
Figure 11:
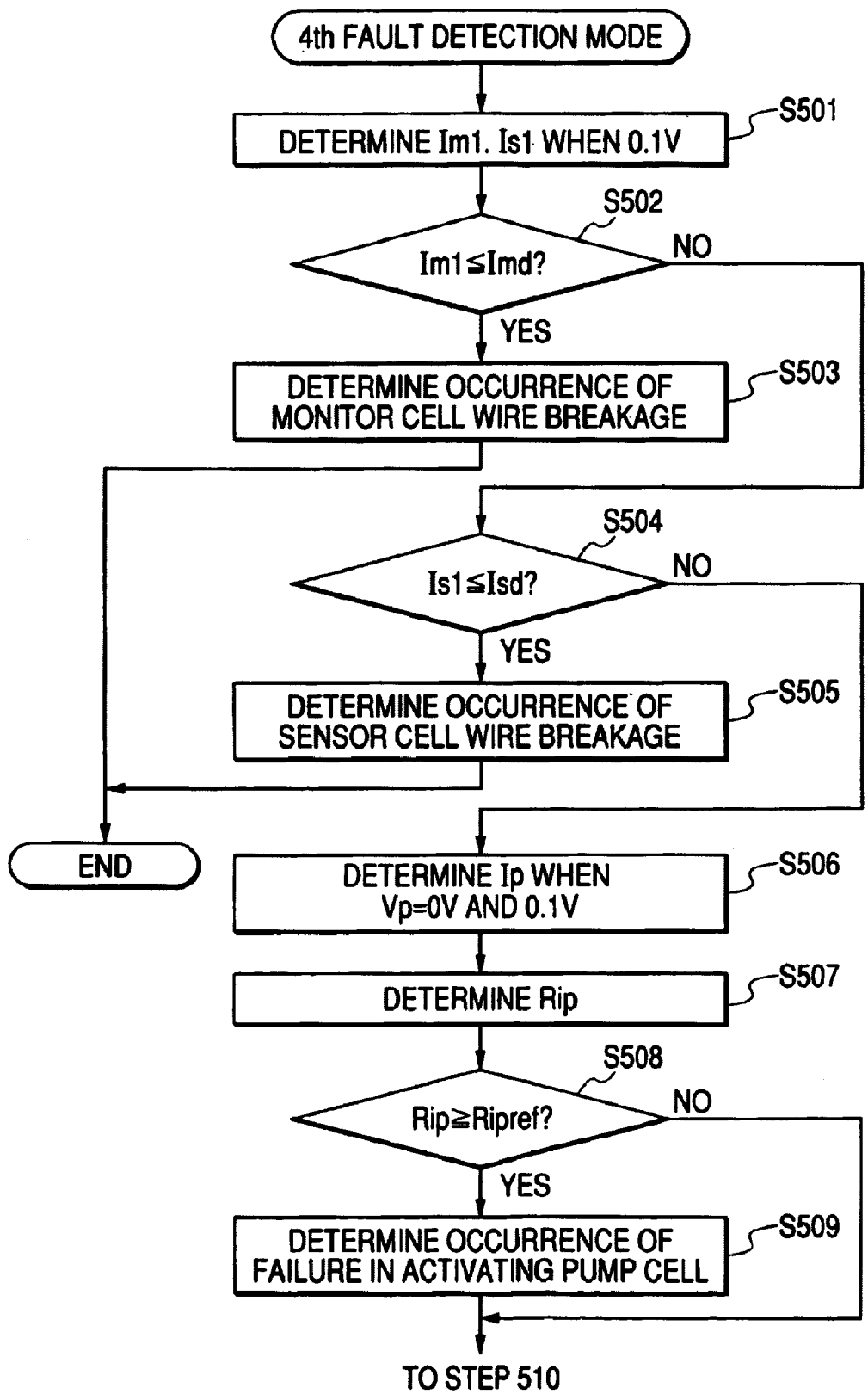
FIGS. 11 and 12 show a flowchart of a sub-program executed to diagnose faults in a NOx sensor when it is unnecessary to measure the concentration of NOx.
Figure 12:
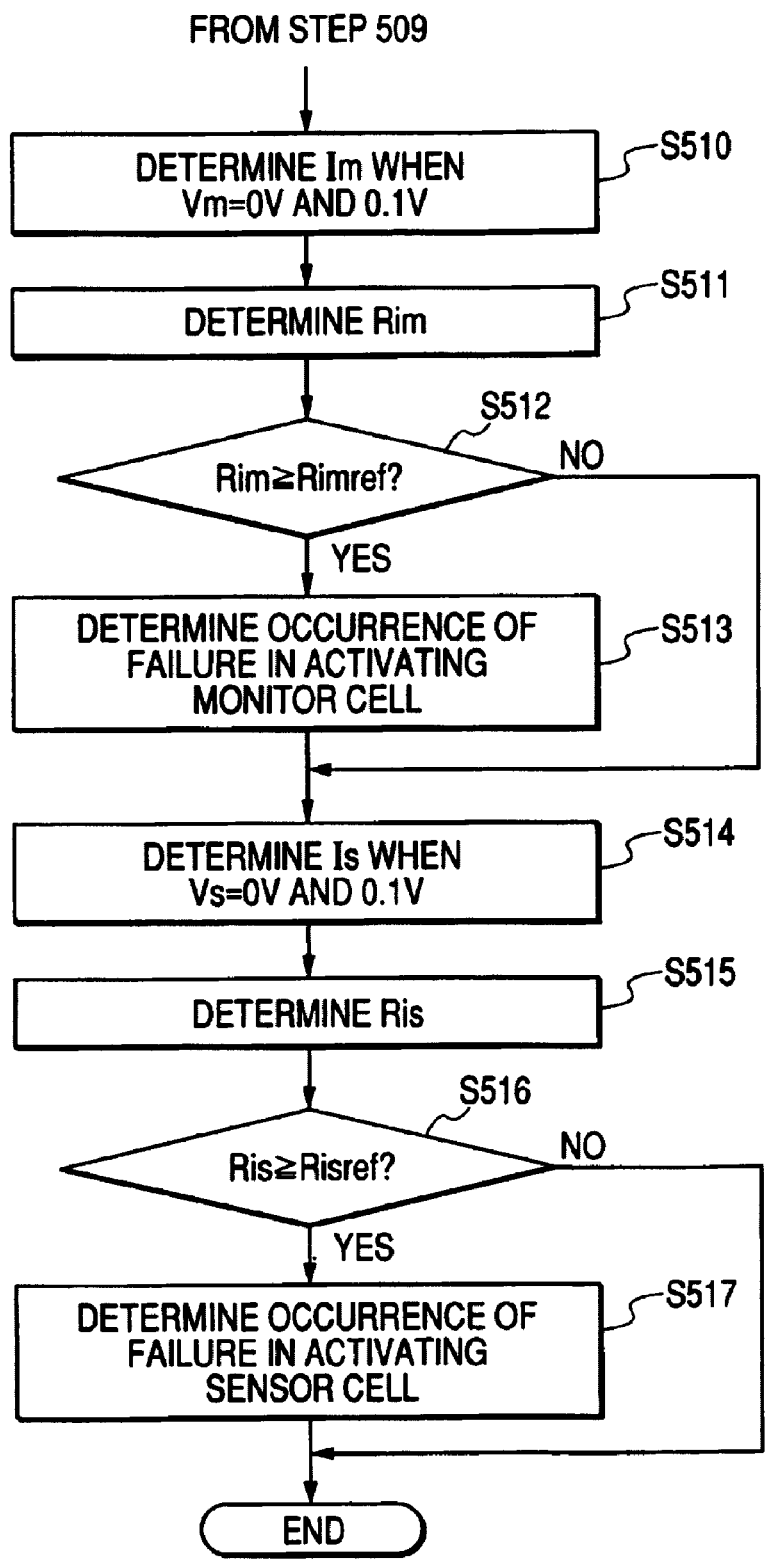

FIGS. 7 to 12 are flowcharts of logical steps or programs stored and performed in the microcomputer 22 of the sensor ECU 21 to detect the above described faults in the NOx sensor 18. The program in FIG. 7 is a main fault detecting program. The program in FIG. 8 is to initiate the first fault detecting mode cyclically which is to be entered when the fuel is being supplied to the engine 10. The program in FIG. 9 is to initiate the second fault detecting mode which is to be entered when the engine 10 is undergoing a fuel cut. The program in FIG. 10 is to initiate the third fault detecting mode which is to be entered when a rich gas is being introduced into the NOx sensor 18. The program in FIGS. 11 and 12 is to initiate the fourth fault detecting mode which is to be entered when it is unnecessary to measure the concentration of NOx.

After entering the main program of FIG. 7, the routine proceeds to step 101 wherein it is determined whether the engine 10 is now undergoing a fuel cut or not. If a YES answer is obtained, then the routine proceeds to step 105 wherein the second fault detecting mode is initiated. Alternatively, if a NO answer is obtained, then the routine proceeds to step 102 wherein it is determined whether a rich gas is being introduced into the NOx sensor 18 or not. If a YES answer is obtained, then the routine proceeds to step 106 wherein the third fault detecting mode is initiated. Alternatively, if a NO answer is obtained, then the routine proceeds to step 103 wherein it is determined whether it is unnecessary to determine the concentration of NOx immediately after the NOx catalyst 16 is reconditioned or not. If a YES answer is obtained, then the routine proceeds to step 107 wherein the fourth fault detecting mode is initiated. Alternatively, if a NO answer is obtained, then the routine proceeds to step 104 wherein the first fault detecting mode is initiated.

When the first fault detecting mode is entered, the routine proceeds to step 201 in FIG. 8 wherein it is determined whether the pump cell current Ip is greater than or equal to the preselected value Ipa (e.g., 5 mA) or not. If a YES answer is obtained, then the routine proceeds to step 202 wherein it is determined that an electrical short has occurred between the electrodes 111 and 112 of the pump cell 110. If such a short has occurred in the pump cell 110, it will result in a difficulty in controlling the concentration of oxygen within the first chamber 144, so that the monitor cell current Im and the sensor cell current Is deviate greatly from correct values. The routine, therefore, terminates.

Alternatively, if a NO answer is obtained in step 201, then the routine proceeds to step 203 wherein it is determined whether the monitor cell current Im is greater than or equal to the preselected value Ima (e.g., 5 μA) or not. If a YES answer is obtained, then the routine proceeds to step 204 wherein it is determined that an electrical short has occurred between the electrodes 121 and 122 of the monitor cell 120. Alternatively, if a NO answer is obtained in step 203, then the routine proceeds to step 205 wherein it is determined whether The sensor cell current Is is greater than or equal to the preselected value Is a (e.g., 5 μA) or not. If a YES answer is obtained, then the routine proceeds to step 206 wherein it is determined that an electrical short has occurred between the electrodes 131 and 122 of the sensor cell 130. If the short has occurred in either of the monitor cell 120 and the sensor cell 130, it will difficult to perform functions thereof correctly. The routine, therefore, terminates.

If no shorts have occurred in all the pump cell 110, the monitor cell 120, and the sensor cell 130, that is, if a NO answer is obtained in step 205, then the routine proceeds to step 207 wherein it is determined whether the monitor cell current Im is greater than or equal to the value Imb (e.g., 1 μA) or not. If a YES answer is obtained, then the routine proceeds to step 208 wherein it is determined that a crack(s) has occurred in a partition wall (i.e., the solid electrolyte layer 141 or 142) of the second chamber 146.

If a NO answer is obtained in step 207, then the routine proceeds to step 209 wherein it is determined whether the amplitude ΔIm of the monitor cell current Im is greater than the value Imc (e.g., 0.5 μA) or not. If a YES answer is obtained, then the routine proceeds to step 210 wherein a crack(s) has occurred in an exhaust gas-exposed partition wall (i.e., the insulating layer 154) of the second air passage 155.

Upon entrance in step 105 in FIG. 7, the routine proceeds to the program in FIG. 9 to initiate the second fault detecting mode which is to be entered during a fuel cut in the engine 10.

First, in step 301 wherein it is determined whether the pump cell current Ip is lower than or equal to the given value Ipb (e.g., 1 mA) or not. If a YES answer is obtained, then the routine proceeds to step 302 wherein it is determined whether the pump cell current Ip is further lower than the given value Ipc (e.g., 0.2 mA) that is smaller than the value Ipb or not. If a NO answer is obtained meaning that Ipc<Ip≦Ipb, then the routine proceeds to step 303 wherein it is determined that the gas inlet 141*a* and/or the porous diffusion layer 147 are clogged. If a YES answer is obtained meaning that Ip≦Ipc, then the routine proceeds to step 304 wherein the wire leading to the electrode 111 or 112 of the pump cell 110 is broken.

If a NO answer is obtained in step 301, then the routine proceeds to step 305 wherein it is determined whether the pump cell current Ip is greater than or equal to the value Ipd (e.g., 3 mA) or not. If a YES answer is obtained, then the routine proceeds to step 306 wherein the crack(s), as indicated either by a or b in FIG. 5(*a*), has been formed in a partition wall of the first chamber 144 (i.e., the solid electrolyte layer 141, the spacer 143, or the solid electrolyte layer 142).

Upon entrance in step 106 in FIG. 7, the routine proceeds to the program in FIG. 10 to initiate the third fault detecting mode which is to be entered during introduction of a rich gas into the NOx sensor 18.

First, in step 401, it is determined whether the pump cell current Ip is greater than the given value Ipe (e.g., −0.3 mA) or not. If a YES answer is obtained, then the routine proceeds to step 402 wherein the crack(s), as indicated by e in FIG. 5(a), has been formed in the partition wall of the air passage 151 (i.e., the insulating layer 150). If a NO answer is obtained in step 401, then the routine terminates.

Upon entrance in step 107 in FIG. 7, the routine proceeds to the program, as illustrated in FIGS. 11 and 12, to initiate the fourth fault detecting mode which is to be entered during undetection of NOx.

First, in step 501, the pump cell-applied voltage Vp is shifted to 0.1V to monitor resulting values Im1 and Is1 of the monitor cell current Im and the sensor cell current Is. The routine proceeds to step 502 wherein it is determined whether the value Im1 of the monitor cell current Im is smaller than the value Imd (e.g., 1 µA) or not. If a YES answer is obtained, then the routine proceeds to step 503 wherein it is determined that the wire leading to the electrode 121 or 122 of the monitor cell 120 is broken. Alternatively, if a NO answer is obtained, then the routine proceeds to step 504 wherein it is determined whether the value Is1 of the sensor cell current Is is smaller than the value Isd (e.g., 1 µA) or not. If a YES answer is obtained, then the routine proceeds to step 505 wherein the wire leading to the electrode 131 or 122 of the sensor cell 130 is broken. If the wire breakage has occurred in either of the monitor cell 120 and the sensor cell 130, that is, after step 503 or 505, the routine terminates.

If a NO answer is obtained in step 504 meaning that the wire breakage has not occurred both in the monitor cell 120 and the sensor cell 130, then the routine proceeds to step 506 wherein the pump cell-applied voltage Vp is shifted to 0V and 0.1V to monitor resulting values Ip00 and Ip01 of the pump cell current Ip. The routine proceeds to step 507 wherein the dc resistance Rip of the pump cell 110 is determined using the values Ip00 and Ip01, as derived in step 506, according to a relation of Rip=0.1/(Ip01−Ip00). The routine proceeds to step 508 wherein it is determined whether the dc resistance Rip is greater than or equal to the reference value Ripref (e.g., 120Ω) or not. If a YES answer is obtained, then the routine proceeds to step 509 wherein a failure has occurred in activating the pump cell 110.

If a NO answer is obtained in step 508 or after step 509, the routine proceeds to step 510 in FIG. 12.

The dc resistance Rim of the monitor cell 120 is determined through steps 510 and 511 in the same manner as used in determining the dc resistance Rip of the pump cell 110. It is determined in step 512 whether the dc resistance Rim is greater than or equal to the reference value Rimref (e.g., 40Ω) or not. If a YES answer is obtained, then the routine proceeds to step 513 wherein a failure has occurred in activating the monitor cell 120.

The dc resistance Ris of the sensor cell 130 is determined through steps 514 and 514 in the same manner as used in determining the dc resistance Rip of the pump cell 110. It is determined in step 516 whether the dc resistance Ris is greater than or equal to the reference value Risref (e.g., 30Ω) or not. If a YES answer is obtained, then the routine proceeds to step 517 wherein a failure has occurred in activating the sensor cell 130. If a NO answer is obtained in step 516 or after step 517, the routine terminates.

After the above described fault in the NOx sensor 18 and types thereof are determined, they are stored in a back-up RAM or an EEPEOM in the microcomputer 22 as diagnostic data. The microcomputer 22 works to correct sensor control schemes, turn on a malfunction indicator lamp, and urges a vehicle operator to replace the NOx sensor 18 based on the types of faults in the NOx sensor 18. For example, if the exhaust gas inlet 141a is clogged or a failure has occurred in activating the cell 110, 120, or 130, but the degree thereof is small or much time has not passed since such a failure is detected, the microcomputer 22 corrects the voltages to be applied to the cells 110, 120, and 130 and continues to use outputs of the cells 110, 120, and 130. If the degree of the fault in the NOx sensor 18 is great or much time has passed since the fault is detected, the microcomputer 22 stops using the output of the cell 110, 120, or 130 and urges the vehicle operator to replace the NOx sensor 18. If the electrode-to-electrode short, the wire breakage, or the cracks have occurred in the cell 110, 120, or 130, the microcomputer 21 stops using the output of the cell 110, 120, or 130 and turns on the malfunction indicator lamp to urge the vehicle operator to replace the NOx sensor 18.

Referring back to FIG. 4(b), the pump cell-applied voltage Vp has an inflection point at which the monitor cell current Im changes suddenly. The value of the pump cell-applied voltage Vp at the inflection point is usually shifted to a higher voltage side when a failure has occurred in activating the pump cell 110, thus resulting in decreased pumping ability thereof. Therefore, when the concentration of NOx is not measured, a determination of whether the activation failure has occurred or not may be made by shifting the pump cell-applied voltage Vp to a lower voltage side and monitoring an instant value of the pump cell-applied voltage Vp when the monitor cell current Im changes suddenly. If the instant value of the pump cell-applied voltage Vp is greater than a standard value, the microcomputer 22 may determine that the failure has occurred in activating the pump cell 110.

Figure 13:
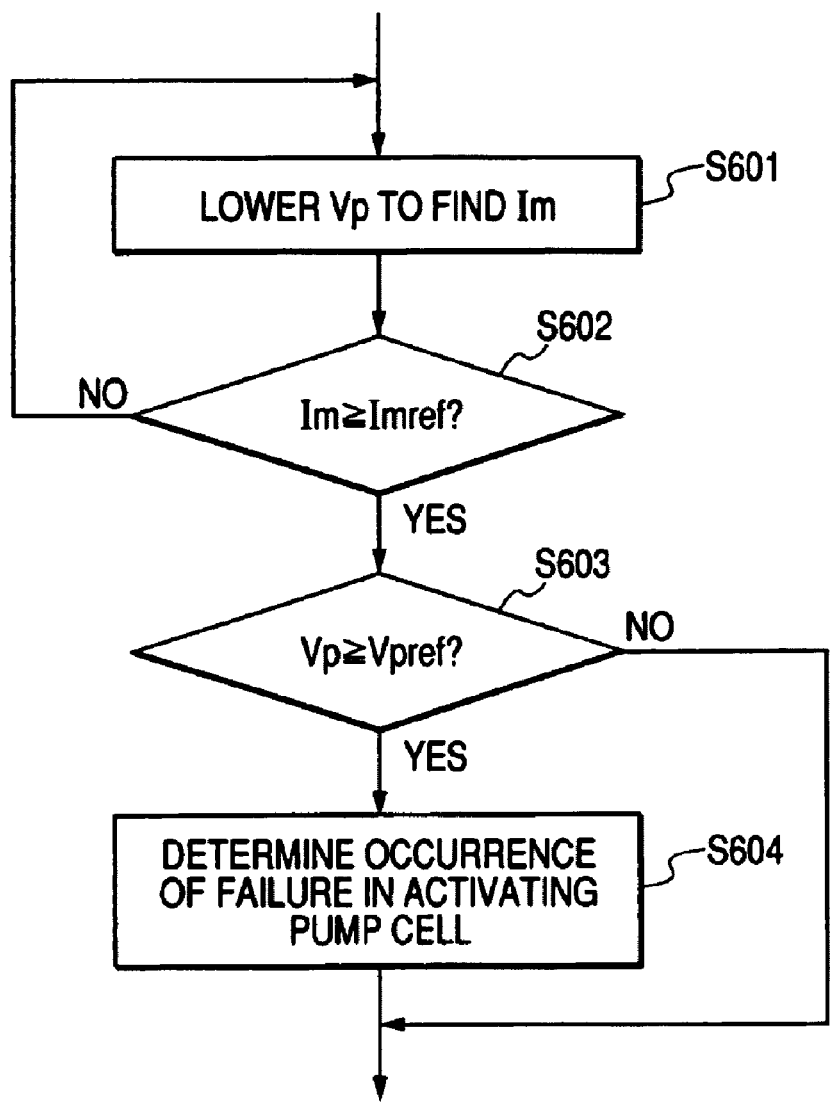
FIG. 13 is a flowchart which shows a modification of the program as illustrated in FIG. 11.

The above determination may be achieved in the microcomputer 22 by executing logical steps, as illustrated in FIG. 13, instead of 506 to 509 in FIG. 11.

In step 601, the pump cell-applied voltage Vp is lowered by, for example, 10 mV to measure a resulting value of the monitor cell current Im. The routine proceeds to step 602 wherein it is determined whether the value of the monitor cell current Im derived in step 601 is greater than or equal to a reference value Imref of, for example, 0.1 µA or not. If a YES answer is obtained, then the routine proceeds to step 603 wherein it is determined whether the value of the pump cell-applied voltage Vp at an instant when the pump cell current Im exceeds the reference value Imref is greater than or equal to a reference value Vpref or not. If a YES answer is obtained, then the routine proceeds to step 604 wherein it is determined that a failure has occurred in activating the pump cell 110. Note that the reference value Vprefused in step 603 depends upon the concentration of oxygen. For example, when the concentration of oxygen is 0%, 10%, and 20%, the reference value Vpref is set to 0.25V, 0.3V, and 0.35V, respectively. When the concentration of oxygen lies between the above percentages, the reference value Vpref may be determined using linear interpolation.

Failures in activating the monitor cell 120 and the sensor cell 130 may also be detected in a manner similar to the above.

The NOx sensor 18 may alternatively be constructed to have only two cells: the pump cell 110 and the sensor cell 130 or more than three cells. The sensor ECU 21 may also be employed in gas concentration sensors such as HC sensors working to measure the concentration of HC in exhaust emissions of the engine or CO sensors working to measure the concentration of CO in exhaust emissions of the engine which are similar in structure to the NOx sensor 18.

Additionally, the sensor ECU 21 may also be employed in oxygen sensors working to measure the concentration of oxygen in exhaust emissions of the engine such as $O_2$ sensors designed to produce an electromotive force as a function of the concentration of oxygen ($O_2$) or A/F sensors designed to produce a limiting current varying linearly with the concentration of oxygen. Such sensors may have a cup-shaped or a laminated sensor element which is made up of a solid electrolyte body, a plurality of electrodes affixed to the solid electrolyte body, and a gas chamber to which at least one of the electrodes is exposed and gas to be measured is admitted and which works to produce an electric signal between two of the electrodes as a function of the amount of oxygen ions traveling through the solid electrolyte body.

The invention may also be employed with gas concentration sensor designed to measure the concentration of gas other than exhaust gas of an automotive engine.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A fault detecting apparatus for a gas concentration sensor which has a sensor element including a solid electrolyte body, a plurality of electrodes affixed to the solid electrolyte body, and a gas chamber to which a gas to be measured is introduced and at least one of the electrode is exposed and works to produce an electrical signal between two of the electrodes as a function of an amount of oxygen ions traveling through the solid electrolyte body, comprising:
   a storage device which stores therein fault detectable conditions in which preselected different types of faults of the gas concentration sensor are allowed to be detected, respectively; and
   a fault detecting circuit working to detect a selected one of the faults stored in said storage device, when one of the fault detectable conditions is encountered during operation of the gas concentration sensor, said fault detecting circuit initiating detection of a corresponding one of the faults based on an output of the gas concentration sensor.

2. A fault detecting apparatus as set forth in claim 1, wherein when one of the fault detectable conditions in which a concentration of oxygen in the gas is known is encountered, said fault detecting circuit initiates detection of a corresponding one of the faults of the gas concentration sensor.

3. A fault detecting apparatus as set forth in claim 2, wherein when one of the fault detectable conditions in which a concentration of oxygen in the gas has increased is encountered, said fault detecting circuit monitor a resulting output of the gas concentration sensor, when the resulting output shows a value smaller than that corresponding to an increase in the concentration of oxygen, said fault detecting circuit determining that one of the faults in introducing the gas into the gas chamber has occurred.

4. A fault detecting apparatus as set forth in claim 3, wherein when the output of the gas concentration sensor is smaller than a threshold used to determine the fault in introducing the gas into the gas chamber, said fault detecting circuit determines as one of the faults that a wire leading to one of the electrodes of the sensor element has been broken.

5. A fault detecting apparatus as set forth in claim 2, wherein when one of the fault detectable conditions in which a concentration of oxygen in the gas has a given higher value is encountered, and a resulting output of the gas concentration sensor is greater than a preselected normal range, said fault detecting circuit determines as one of the faults that a cark is formed in a partition wall defining the gas chamber.

6. A fault detecting apparatus as set forth in claim 2, wherein the gas introduced into the gas chamber is an exhaust gas of an internal combustion engine, and wherein when one of the fault detectable conditions in which the engine is undergoing a fuel cut is encountered, said fault detecting circuit initiates the detection of the corresponding one of the faults of the gas concentration sensor.

7. A fault detecting apparatus as set forth in claim 1, wherein the gas concentration sensor also includes a reference oxygen gas chamber facing the gas chamber across the solid electrolyte body, and wherein when one of the fault detectable conditions in which a concentration of oxygen in the gas changes to a given lower value is encountered, and a resulting value of the output of the gas concentration sensor is different from one corresponding to the given lower value, said fault detecting circuit determines as one of the faults that a crack is formed in a partition wall defining the reference oxygen gas chamber.

8. A fault detecting apparatus as set forth in claim 7, wherein the gas introduced into the gas chamber is an exhaust gas of an internal combustion engine, and wherein when one of the fault detectable conditions in which a rich air-fuel ratio corresponding exhaust gas is introduced into the gas chamber is encountered, said fault detecting circuit initiates detection of said fault.

9. A fault detecting apparatus as set forth in claim 1, wherein when one of the fault detectable conditions in which a time when it is unnecessary to measure a concentration of the gas is reached is encountered, said fault detecting circuit increases and decreases a voltage applied across the two of the electrodes of the sensor element to determine a resistance value of the sensor element, when the resistance value is greater than a given value, said fault detecting circuit determining as one of the faults that a failure has occurred in activating the sensor element.

10. A fault detecting apparatus as set forth in claim 1, wherein when one of the fault detectable conditions in which the output of the gas concentration sensor increases up to near a limit of a current capacity of a driver circuit used to actuate the sensor element during operation of the gas concentration sensor is encountered, said fault detecting circuit determines as one of the faults that an electrical short has occurred between the electrodes of the sensor element.

11. A fault detecting apparatus for a gas concentration sensor which has a sensor element including a first chamber into which a gas to be measured is introduced, a second chamber leading to the first chamber, a first cell which works to pump oxygen into and out of the first chamber selectively to keep a concentration of oxygen at a given level within the first chamber and produces an electrical signal as a function of the concentration of oxygen, and a second cell which works to produce an electrical signal as a function of a concentration of a specified component of the gas flowing from the first chamber into the second chamber, comprising:

a storage device which stores therein fault detectable conditions in which preselected different types of faults of the gas concentration sensor are allowed to be detected, respectively; and a fault detecting circuit working to detect a selected one of the faults stored in said storage device, when one of the fault detectable conditions is encountered during operation of the gas concentration sensor, said fault detecting circuit initiating detection of a corresponding one of the faults based on outputs of the first and second cells.

12. A fault detecting apparatus as set forth in claim 11, wherein when one of the fault detectable conditions in which the concentration of oxygen in the gas is known is encountered, said fault detecting circuit initiates detection of a corresponding one of the faults of the gas concentration sensor using the output of the first cell.

13. A fault detecting apparatus as set forth in claim 12, wherein when one of the fault detectable conditions in which the concentration of oxygen in the gas has increased is encountered, said fault detecting circuit monitors a resulting output of the first cell, when the resulting output shows a value smaller than that corresponding to an increase in the concentration of oxygen, said fault detecting circuit determining that one of the faults in introducing the gas into the first chamber has occurred.

14. A fault detecting apparatus as set forth in claim 13, wherein when the output of the first cell is smaller than a threshold used to determine the fault in introducing the gas into the first chamber, said fault detecting circuit determines as one of the faults that a wire leading to an electrode of the first cell has been broken.

15. A fault detecting apparatus as set forth in claim 12, wherein when one of the fault detectable conditions in which the concentration of oxygen in the gas has a given higher value is encountered, and a resulting output of the first cell is greater than a preselected normal range, said fault detecting circuit determines as one of the faults that a crack is formed in a partition wall defining the first chamber.

16. A fault detecting apparatus as set forth in claim 12, wherein the gas introduced into the gas chamber is an exhaust gas of an internal combustion engine, and wherein when one of the fault detectable conditions in which the engine is undergoing a fuel cut is encountered, said fault detecting circuit initiates the detection of the corresponding one of the faults of the gas concentration sensor.

17. A fault detecting apparatus as set forth in claim 11, wherein the sensor element also includes a reference oxygen gas chamber facing the first chamber across the first cell, and wherein when one of the fault detectable conditions in which the concentration of oxygen in the gas changes to a given lower value is encountered, and a resulting value of the output of the first cell is different from one corresponding to the given lower value, said fault detecting circuit determines as one of the faults that a crack is formed in a partition wall defining the reference oxygen gas chamber.

18. A fault detecting apparatus as set forth in claim 17, wherein the gas introduced into the first chamber is an exhaust gas of an internal combustion engine, and wherein when the one of the fault detectable conditions in which a rich air-fuel ratio corresponding exhaust gas is introduced into the gas chamber is encountered, said fault detecting circuit initiates detection of said fault.

19. A fault detecting apparatus as set forth in claim 11, wherein when one of the fault detectable conditions in which a time when it is unnecessary to measure the concentration of the specified component of the gas is reached is encountered, said fault detecting circuit increases and decreases a voltage applied across electrodes of one of the first and second cells to determine a resistance value of the one of the first and second cells, when the resistance value is greater than a given value, said fault detecting circuit determining as one of the faults that a failure has occurred in activating the one of the first and second cells.

20. A fault detecting apparatus as set forth in claim 11, wherein when one of the fault detectable conditions in which the concentration of oxygen in the first chamber is kept by the first cell at the given level is encountered, and when the output of the second cell is greater than a given normal range, said fault detecting circuit determines as one of the faults that a crack is formed in a partition wall defining the second chamber.

21. A fault detecting apparatus as set forth in claim 11, wherein when one of the fault detectable conditions in which the output of one of the first and second cells increases up to near a limit of a current capacity of a driver circuit used to actuate the one of the first and second cells during operation of the gas concentration sensor is encountered, said fault detecting circuit determines as one of the faults that an electrical short has occurred between electrodes of the one of the first and second cells.

22. A fault detecting apparatus as set forth in claim 11, wherein when one of the fault detectable conditions in which a voltage to be applied to the first cell is decreased below that used to measure the concentration of the specified gas component is encountered, and when a resulting value of the output of the second cell is smaller than a given value, said fault detecting circuit determines as one of the faults that a wire leading to an electrode of the second cell is broken.

23. A fault detecting apparatus as set forth in claim 11, wherein when one of the fault detectable conditions in which a time when it is unnecessary to measure the concentration of the specified component of the gas is reached is encountered, said fault detecting circuit shifts a voltage applied to the first cell to a lower level to find a voltage level applied to the first cell at which a value of the output of the second cell changes suddenly in relation to a change in the voltage applied to the first cell, when the found voltage level is greater than a given normal level, said fault detecting circuit determining as one of the faults that a failure has occurred in activating the first cell.

24. A fault detecting apparatus as set forth in claim 11, wherein the sensor element also includes a third cell which produces an output as a function of a concentration of oxygen within the second chamber, and the gas concentration sensor is designed to control a voltage applied to the first cell, and wherein when a selected one of the fault detectable conditions is encountered during operation of the gas concentration sensor, said fault detecting circuit initiates the detection of a corresponding one of the faults based on the output of the third cell.

25. A fault detecting apparatus as set forth in claim 24, wherein when one of the fault detectable conditions in which a time when it is unnecessary to measure the concentration of the specified component of the gas is reached is encountered, said fault detecting circuit increases and decreases a voltage applied to the third cell to find a resistance value of the third cell, when the resistance value is greater than a given value, said fault detecting circuit determining as one of the faults that a failure has occurred in activating the third cell.

26. A fault detecting apparatus as set forth in claim 24, wherein when one of the fault detectable conditions in which the concentration of oxygen in the first chamber is kept by the first cell at the given level is encountered, and when the output of the third cell is greater than a given normal range, said fault detecting circuit determines as one of the faults that a crack is formed in a partition wall defining the second chamber.

27. A fault detecting apparatus as set forth in claim 24, wherein when one of the fault detectable conditions in which the output of the third cell increases up to near a limit of a current capacity of a driver circuit used to actuate the third cell during operation of the gas concentration sensor is encountered, said fault detecting circuit determines as one of the faults that an electrical short has occurred between electrodes of the third cell.

28. A fault detecting apparatus as set forth in claim 24, wherein when one of the fault detectable conditions in which a voltage to be applied to the first cell is decreased below that used to measure the concentration of the specified gas component is encountered, and when a resulting value of the output of the third cell is smaller than a given value, said fault detecting circuit determines as one of the faults that a wire leading to an electrode of the third cell is broken.

29. A fault detecting apparatus as set forth in claim 24, wherein when one of the fault detectable conditions in which a time when it is unnecessary to measure the concentration of the specified component of the gas is reached is encountered, said fault detecting circuit shifts a voltage applied to the first cell to a lower level to find a voltage level applied to the first cell at which a value of the output of the third cell changes suddenly in relation to a change in the voltage applied to the first cell, when the found voltage level is greater than a given normal level, said fault detecting circuit determining as one of the faults that a failure has occurred in activating the third cell.

* * * * *